US007148032B2

(12) United States Patent
Stringer et al.

(10) Patent No.: US 7,148,032 B2
(45) Date of Patent: Dec. 12, 2006

(54) PHOSPHOLIPASE

(75) Inventors: Mary Ann Stringer, Soeborg (DK); Tine Muxoll Fatum, Alleroed (DK); Shamkant Anant Patkar, Lyngby (DK)

(73) Assignees: Novozymes A/S, Bagsvaerd (DK); Christian Hansen A/S, Hoersholm (DE)

( * ) Notice: Subject to any disclaimer, the term of this patent is extended or adjusted under 35 U.S.C. 154(b) by 405 days.

(21) Appl. No.: 10/831,043

(22) Filed: Apr. 23, 2004

(65) Prior Publication Data

Related U.S. Application Data

(60) Provisional application No. 60/496,158, filed on Aug. 19, 2003, provisional application No. 60/467,865, filed on May 5, 2003.

(30) Foreign Application Priority Data

| | | |
|---|---|---|
| Apr. 28, 2003 | (DK) | 2003 00634 |
| Aug. 14, 2003 | (DK) | 2003 01163 |

(51) Int. Cl.
*C12Q 1/34* (2006.01)
*C12N 9/16* (2006.01)

(52) U.S. Cl. .................... 435/18; 435/196; 435/252.3; 435/320.1; 536/23.2

(58) Field of Classification Search .................. 435/18, 435/196, 252.3, 320.1; 536/23.2
See application file for complete search history.

(56) References Cited

U.S. PATENT DOCUMENTS 6,399,121 B1 6/2002 Nielsen

FOREIGN PATENT DOCUMENTS

| | | |
|---|---|---|
| JP | 06327468 | 11/1994 |
| WO | WO 98/26057 | 6/1998 |
| WO | WO 99/03962 | 1/1999 |
| WO | WO 99/53769 | 10/1999 |
| WO | WO 00/54601 | 9/2000 |
| WO | WO 02/00852 | 1/2002 |

OTHER PUBLICATIONS

Accession No. XP-002259297, (Apr. 2, 2003).
Accession No. XP-002259299, (Jul. 6, 2000).
Accession No. XP-002259298, (Jan. 23, 2002).
Soragni et al., The EMBO Journal, vol. 20, No. 18, pp. 5079-5090, (2001).

*Primary Examiner*—Tekchand Saidha
(74) *Attorney, Agent, or Firm*—Jason Garbell

(57) ABSTRACT

The present invention is related to a method for producing a phospholipase by processing an expressed fungal peptide and to certain specified phospholipases. Furthermore the invention provides a method for producing cheese with a phospholipase.

13 Claims, 1 Drawing Sheet

PHOSPHOLIPASE

CROSS-REFERENCE TO RELATED APPLICATIONS

This application claims the benefit of U.S. provisional application Nos. 60/467,865, filed May 5, 2003, and 60/496,158, filed, Aug. 19, 2003, and priority of Danish Patent Application Nos. PA 2003 00634, filed Apr. 28, 2003, and PA 2003 001163, filed Aug. 14, 2003 the contents of which are fully incorporated herein by reference.

FIELD OF THE INVENTION

The present invention relates to a method of hydrolyzing a phospholipid, a method of producing a phospholipase, a method of making cheese, and to a phospholipase.

BACKGROUND OF THE INVENTION

Soragni, E., et al. (2001) EMBO J. 20: 5079–5090 discloses a phospholipase (TbSP1) from *Tuber borchii* and the nucleotide sequence of a cDNA of a gene encoding it. The following peptide sequence are published in the indicated sources, derived from the indicated source organism:

COGEME Phytopathogenic Fungi and Oomycete EST Database, Unisequence ID: VD0100C34, *Verticillium dahliae.*

NCBI Protein database, gi:18307435, *Neurospora crassa*

NCBI Protein database, gi:16519372, *Helicosporum* sp. HN1

WO 0056762, SEQ ID NO: 5954, *Aspergillus oryzae*

TREMBL Protein database, EAA28927, *Neurospora crassa* U.S. Pat. No. 6,399,121 discloses the use of phospholipase in cheese making.

SUMMARY OF THE INVENTION

The inventors have analyzed known sequence data for fungal Group XIII phospholipases A2, and they have identified additional sequences, either from published sequence data or by screening for relevant sequences from natural sources. By expressing genes encoding fungal Group XIII phospholipases A2 in a suitable host organism they found that the expressed sequences consist of a core peptide coupled to a peptide sequence at the N- or C-terminal side, or both, and that expression of the gene in a suitable host organism can lead to cleavage of the expressed peptide to obtain the core peptide without any peptide extension at the N- or C-terminal. They further found that the core peptide without any peptide extension(s) has a significantly higher phospholipase activity than the core peptide linked to the peptide extension(s). Finally, they found that the core peptide discovered by this method is similar in length and sequence to a known mature peptide from *Helicosporium* sp. (Wakatsuki, S. et al. (2001) Biochim. Biophys. Acta 1522: 74–81) of unknown function, and to bacterial Group XIII phospholipases A2, which lack peptide extensions other than secretion signals (Sugiyama, M. et. al. (2002) J. Biol. Chem. 277:20051–20058).

The inventors additionally found that phospholipase sharing the active site sequence similarity and cysteine residue conservation of fungal Group XIII phospholipase A2 is useful in cheese making.

Additionally, the inventors discovered and isolated a gene encoding a novel phospholipase from *Fusarium venenatum* A3/5, which was originally deposited as *Fusarium graminearum* ATCC 20334 and recently reclassified as *Fusarium venenatum* by Yoder and Christianson, 1998, Fungal Genetics and Biology 23: 62–80; and O'Donnell et al., 1998, Fungal Genetics and Biology 23: 57–67. The phospholipase belongs to the fungal/bacterial group XIII PLA2 as defined by Soragni et al., The EMBO Journal, 20 (2001), 5079–5090. The inventors also cloned the novel phospholipase encoding gene into an *E. coli* strain, and used the cloned gene to make a construct for expressing the *Fusarium* phospholipase gene in *Aspergillus oryzae*. The inventors transformed *Aspergillus oryzae* with this construct, and isolated the phospholipase from transformed *Aspergillus* cells.

Accordingly, the invention provides a method of producing a phospholipase which comprises processing an expressed fungal peptide so as to cleave off a peptide from the C-terminal end and/or a peptide from the N-terminal end to obtain a core peptide, wherein the core peptide comprises:

a) the amino acid sequence given by amino acids 146–153 of SEQ ID NO: 1, amino acids 87–94 of SEQ ID NO: 3, or amino acids 79–86 of SEQ ID NO: 12; or a sequence identical to any of these amino acid sequences except for the substitution of a single amino acid with another amino acid; and b) at least two cysteine residues located on the N-terminal side of the sequence given in a); and c) at least two cysteine residues located on the C-terminal side of the sequence given in a).

The invention also provides a method for hydrolyzing a phospholipid with a phospholipase of the invention. Furthermore the invention provides a method for producing cheese by contacting cheese milk or a fraction of cheese milk with a phospholipase and producing cheese from the cheese milk.

Finally, the invention provides phospholipase which is a polypeptide having an amino acid sequence which is at least 80% identical with certain specified sequences.

DETAILED DESCRIPTION OF THE INVENTION

Expressed Peptide

Figure 1:
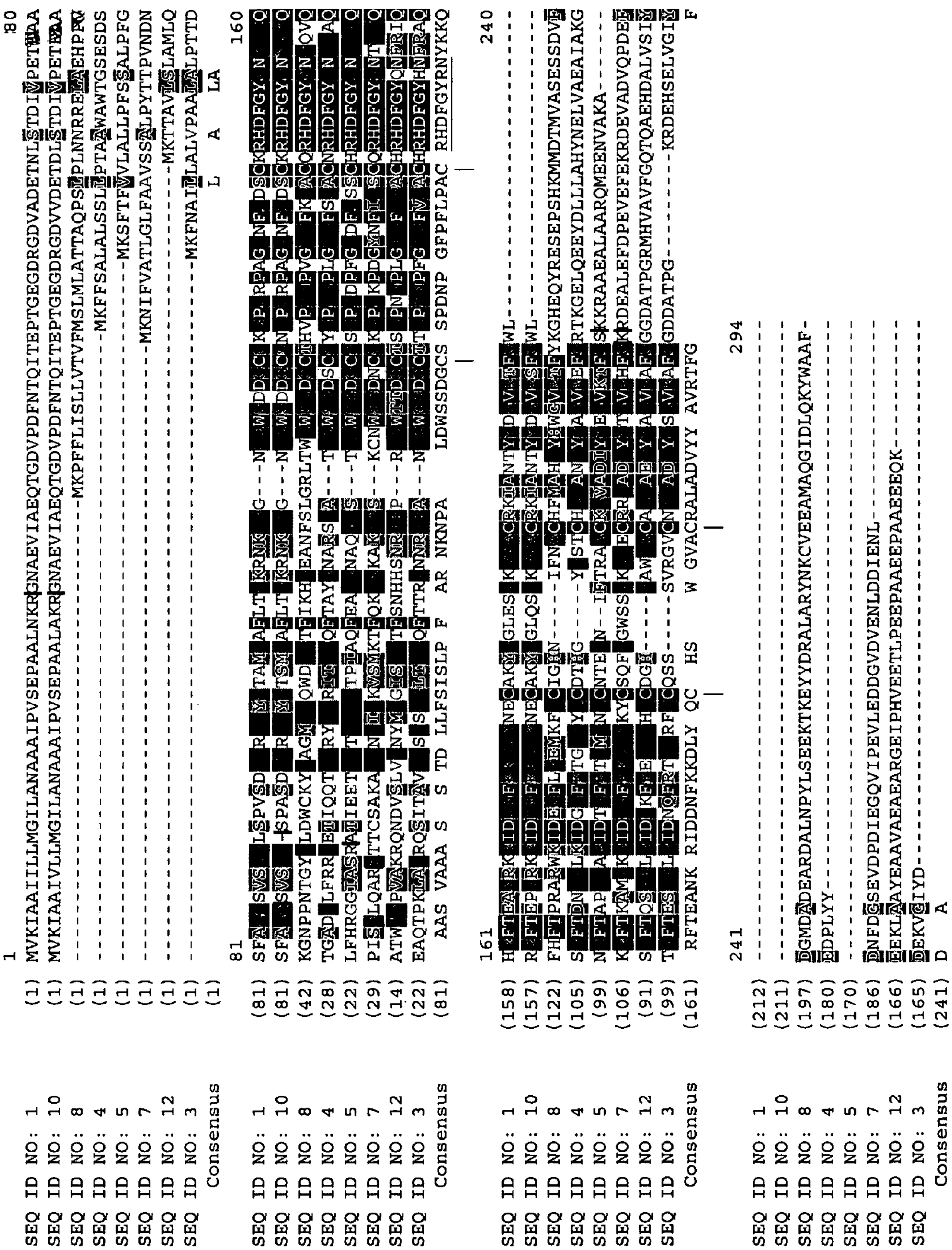
FIG. 1 shows an alignment of amino acid sequences of fungal group XIII phospholipases A2, showing processing sites (|) where known. The active site consensus is underlined. Conserved cysteine residues are indicated with | under the consensus. Alignment was made with the AlignX program of the Vector NTI program suite v8. The algorithm used is ClustalW with the blosum62mt2 matrix and AlignX default settings.

The invention uses an expressed fungal peptide belonging to a group defined by the active site sequence similarity and cysteine residue conservation used in the definition of the group "fungal/bacterial group XIII phospholipase A2" given by Soragni, E., et al. (2001) EMBO J. 20: 5079–5090. The peptide is fungal, e.g. derived from *Tuber, Verticillium, Neurospora, Helicosporum*, or *Aspergillus*, particularly *T. borchii, T. albidum, V. dahliae, V. tenerum, N. crassa, Helicosporium* sp. HN1 or *A. oryzae.*

The peptide may have phospholipase activity, e.g. phospholipase A activity, such as phospholipase A1 and/or phospholipase A2 activity.

Some particular examples are known peptides having amino acid sequences listed in the sequence listing as follows. The source organisms and literature references are also indicated:

SEQ ID NO:1. *Tuber borchii*. Soragni, E., et al. (2001) EMBO J. 20: 5079–5090

SEQ ID NO: 3. *Verticillium dahliae*. COGEME Phytopathogenic Fungi and Oomycete EST Database, Unisequence ID: VD0100C34.

SEQ ID NO: 4. *Neurospora crassa*. NCBI Protein database, gi:18307435.

SEQ ID NO: 5. *Helicosporum* sp. HN1. NCBI Protein database, gi:16519372.

SEQ ID NO: 7. *Aspergillus oryzae*. WO 0056762, SEQ ID NO: 5954.

SEQ ID NO 8. *Neurospora crassa*. TREMBL Protein database, EAA28927

Further, the following fungal phospholipases having the indicated sequences were isolated by the inventors from natural sources purchased from public collections or collected in the indicated country and year:

SEQ ID NO: 10. *Tuber albidum*. Purchased from Centraalbureau voor Schimmelcultures, Utrecht, The Netherlands, isolate CBS272.72

SEQ ID NO: 12. *Verticillium tenerum*. Ireland, 1996

The inventors inserted the gene from *T. albidum* (SEQ ID NO: 9) into *E. coli* and deposited the clone under the terms of the Budapest Treaty on the 12 Feb. 2003. The deposit was made at the Deutsce Sammlung von Mikroorganismen und Zellkulturen (DSMZ), Mascheroder Weg 1b, D-38124 Braunschweig, Germany, and was accorded deposit number DSM 15441.

In one embodiment the invention provides a phospholipase which is a polypeptide having an amino acid sequence which is at least 80%, such as at least 85%, preferably 90%, more preferably at least 95%, identical with amino acids 91–210 in SEQ ID NO: 10 (*T. albidum*), amino acids 92–211 in SEQ ID NO: 1 (*T. borchii*), amino acids 30–137 in SEQ ID NO: 12 (*V. tenerum*), amino acids 38–145 in SEQ ID NO: 3 (*V. dahliae*), amino acids 44–151 in SEQ ID NO: 4 (*N. crassa*), amino acids 37–157 in SEQ ID NO: 7 (*A. oryzae*), or amino acids 58–168 in SEQ ID NO: 8 (*N. crassa*).

Peptide Processing

By analyzing the phospholipase sequences in the sequence listing, the inventors found that each expressed amino acid sequence consists of a signal peptide, a core peptide, and additionally a peptide sequence with unknown function attached to the C- or N-terminal, or both, of the core peptide.

Core Peptide

The core peptides are characterized by the same active site sequence similarity and cysteine residue conservation observed by Soragni, E., et al. (2001) EMBO J. 20: 5079–5090 for the fungal/bacterial group XIII phospholipase A2.

In a preferred embodiment of the invention the core peptides comprises: a) the sequence given by amino acids 146–153 of SEQ ID NO: 1, amino acids 87–94 of SEQ ID NO: 3, or amino acids 79–86 of SEQ ID NO: 12; or a sequence identical to any of these amino acid sequences except for the substitution of a single amino acid with another amino acid; and b) two cysteine residues located on the N-terminal side of the sequence given in a); and c) two cysteine residues located on the C-terminal side of the sequence given in a).

One of the cysteine residues located on the N-terminal side of the sequence given in a), may e.g. be separated from the sequence given in a) by 0–5 amino acids, such as 0–3 amino acids, preferably 0–2 amino acids, and even more preferably 1 amino acid. Another of the cysteine residues located on the N-terminal side of the sequence given in a) may e.g. be separated from the sequence given in a) by 14–20 amino acids, such as 15–19 amino acids, preferably 16–18 amino acids, and even more preferably 17 amino acids.

One of the cysteine residues located on the C-terminal side of the sequence given in a), may e.g. be separated from the sequence given in a) by 22–29 amino acids, such as 23–28 amino acids, preferably 24–27 amino acids, and even more preferably 25–26 amino acids. Another of the cysteine residues located on the C-terminal side of the sequence given in a) may e.g. be separated from the sequence given in a) by 27–49 amino acids, such as 29–46 amino acids, preferably 30–43 amino acids, even more preferably 32–42 amino acids, and most preferably 35–40 amino acids.

In a preferred embodiment the core peptide comprises four cysteine residues aligning with the cysteine residues of SEQ ID NO:1 with amino acid numbers 128, 144, 180, and 194, respectively, when the complete expressed phospholipase sequence is aligned simultaneously with the sequences given in SEQ ID NO: 1, SEQ ID NO: 3, SEQ ID NO: 4, SEQ ID NO: 5, SEQ ID NO: 7, SEQ ID NO: 8, SEQ ID NO: 10, and SEQ ID NO: 12.

According to the invention, the expressed polypeptide is cleaved so as to separate the core peptide from the attached peptide(s). The cleavage may be done in vivo by expressing it in a suitable filamentous fungal host or in vitro, e.g. by a treatment with a suitable protease such as e.g. Kex2.

The cleavage points may be found within 11 amino acids of a sequence which is FG or within 10 amino acids of a sequence which is a Kex2 site. Kex2 sites are e.g. RR, KR, KK or RK. In one embodiment the core peptide has a length of 100–150 amino acids, such as 110–140 amino acids, 115–133 amino acids, 118–129 amino acids, or 118–126 amino acids.

In one embodiment of the invention the expressed phospholipase is cleaved within 0–18 amino acids, such as 3–16 amino acids, preferably 5–14 amino acids on the N-terminal side of the sequence aligning with amino acids 97–101 of SEQ ID NO: 1, when the complete expressed phospholipase sequence is aligned simultaneously with the sequences given in SEQ ID NO: 1, SEQ ID NO: 3, SEQ ID NO: 4, SEQ ID NO: 5, SEQ ID NO: 7, SEQ ID NO: 8, SEQ ID NO: 10, and SEQ ID NO: 12.

In a preferred embodiment the expressed phospholipase is cleaved within 0–11 amino acids, such as 0–9 amino acids, preferably 0–7 amino acids, on the C-terminal side of the sequence aligning with amino acids 204–209 of SEQ ID NO: 1, when the complete expressed phospholipase sequence is aligned simultaneously with the sequences given in SEQ ID NO: 1, SEQ ID NO: 3, SEQ ID NO: 4, SEQ ID NO: 5, SEQ ID NO: 7, SEQ ID NO: 8, SEQ ID NO: 10, and SEQ ID NO: 12.

In a preferred embodiment the processed phospholipase has a specific phospholipase activity, which is higher than the activity of the expressed peptide before processing, e.g. in one embodiment the specific phospholipase activity is at least 2 times, more preferably at least 5 times, most preferably at least 10 times the specific phospholipase activity of the expressed peptide before processing. In one embodiment of the invention the expressed peptide does not have measurable phospholipase activity before processing.

Phospholipase activity may e.g. be measured in the LEU assay by hydrolyzing soy lecithin (L-alfa-phosphotidylcholine) at pH 8.0 and 40° C. for 2 minutes. Phospholipase activity is expressed as the rate of titrant consumption (0.1 M NaOH) necessary for keeping constant pH, relative to a standard.

Expression in Filamentous Fungal Host Cell

The filamentous fungal host cell may e.g. be a cell of *Acremonium, Aspergillus, Fusarium, Humicola, Myceliophthora, Neurospora, Penicillium, Rhizomucor, Thermomyces, Thielavia, Tolypocladium*, or *Trichoderma*, particularly *A. awamori, A. foetidus, A. japonicus, A. nidulans, A. niger, A. oryzae. F. bactridioides, F. cerealis, F. crookwellense, F. culmorum, F. graminearum, F. graminum, F. heterosporum, F. negundi, F. oxysporum, F. reticulatum, F. roseum, F. sambucinum, F. sarcochroum, F. sporotrichioides, F. sulphureum, F. torulosum, F. trichothecioides, F. venenatum, H. insolens, M. thermophila, N. crassa, P. purpurogenum, R. miehei, Thermomyces lanuginosus, Thielavia terrestris, Trichoderma harzianum, Trichoderma koningii, Trichoderma longibrachiatum, Trichoderma reesei*, or *Trichoderma viride.*

In a preferred embodiment the host organism is a strain of *Aspergillus, Fusarium*, or *Trichoderma*, particularly *A. niger, A. oryzae, F. venenatum, F. sambucinum* or *F. cerealis*

The transformation, cultivation, expression, recovery may be performed by conventional methods, e.g. by the general methods described in EP 238023, EP 305216, WO 9600787, EP 244234 or T. Christensen et al., BioTechnology, vol. 6, December 1988, 1419–22.

Phospholipase Polypeptide and DNA

In one embodiment, the present invention relates to polypeptides having phospholipase activity and where the polypeptides comprises, preferably consists of, an amino acid sequence which has a degree of identity to amino acids 29 to 149 of SEQ ID NO: 16 (i.e., the mature polypeptide) of at least 80%, such as at least 85%, even more preferably at least 90%, most preferably at least 95%, e.g. at least 96%, such as at least 97%, and even most preferably at least 98%, such as at least 99%.

Preferably, the polypeptides comprise the amino acid sequence of SEQ ID NO: 16; an allelic variant thereof; or a fragment thereof that has phospholipase activity. In another preferred embodiment, the polypeptide of the present invention comprises amino acids 29 to 149 of SEQ ID NO: 16. In a further preferred embodiment, the polypeptide consists of amino acids 29 to 149 of SEQ ID NO: 16.

The present invention also relates to a polynucleotide comprising, preferably consisting of, a nucleotide sequence which has at least 80% identity with nucleotides 133 to 495 of SEQ ID NO: 15. Preferably, the nucleotide sequence has at least 85% identity, such as at least 90% identity, more preferably at least 95% identity, such as at least 96% identity, e.g. at least 97% identity, even more preferably at least 98% identity, such as at least 99% with nucleotides 133 to 495 of SEQ ID NO: 15. Preferably, the nucleotide sequence encodes a polypeptide having phospholipase activity.

The phospholipase may be derived from a strain of *Fusarium*, particularly *F. venenatum*, using probes designed on the basis of the DNA sequences in this specification. In one embodiment the phospholipase has phospholipase A activity.

The phospholipase may be produced by transforming a suitable host cell with a DNA sequence encoding the phospholipase, cultivating the transformed organism under conditions permitting the production of the enzyme, and recovering the enzyme from the culture.

The host organism is preferably a eukaryotic cell, in particular a fungal cell, such as a yeast cell or a filamentous fungal cell, such as a strain of *Aspergillus, Fusarium, Trichoderma* or *Saccharomyces*, particularly *A. niger, A. oryzae, F. venenatum, F. sambucinum, F. cerealis* or *S. cerevisiae*, e.g. a glucoamylase-producing strain of *A. niger* such as those described in U.S. Pat. No. 3,677,902 or a mutant thereof. The production of the phospholipase in such host organisms may be done by the general methods described in EP 238,023 (Novo Nordisk), WO 96/00787 (Novo Nordisk) or EP 244,234 (Alko).

The expression vector of the invention typically includes control sequences functioning as a promoter, a translation initiation signal, and, optionally, a selectable marker, a transcription terminator, a repressor gene or various activator genes. The vector may be an autonomously replicating vector, or it may be integrated into the host cell genome.

Sequence Alignment and Identity

Nucleotide sequences may be aligned with the AlignX application of the Vector NTI Program Suite 7.0 using the default settings, which employ a modified ClustalW algorithm (Thompson, J. D., Higgins, D. G., and Gibson T. J. (1994) Nuc. Acid Res. 22: 4673–4680), the swgapdnarnt score matrix, a gap opening penalty of 15 and a gap extension penalty of 6.66.

Amino acid sequences may be aligned with the AlignX application of the Vector NTI Program Suite v8 using default settings, which employ a modified ClustalW algorithm (Thompson, J. D., Higgins, D. G., and Gibson T. J., 1994), the blosum62mt2 score matrix, a gap opening penalty of 10 and a gap extension penalty of 0.1.

In one embodiment of the invention alignments of sequences and calculation of homology scores are done using the Lipman-Pearson Method (Lipman, D. J. and W. R. Pearson (1985) Rapid and sensitive protein similarity searches. Science 227: 1435–1441) using a PAM250 residue weight table (Dayhoff, M. O., R. M. Schwartz, and B. C. Orcutt (1978) A model of evolutionary change in proteins. In Dayhoff, M. O. (ed.), Atlas of Protein Sequence and Structure. National Biomedical Research Foundation. Washington, D.C. Vol 5. Suppl. 3: pp. 345–358) and the default settings of the MegAlign program, v4.03, in the Lasergene software package (DNASTAR Inc., 1228 South Park Street, Madison, Wis. 53715). The default settings are a K-tuple of 2, gap penalty of 4, and a gap length penalty of 12.

Phospholipid Hydrolysis

The invention may be used in the hydrolysis of any phospholipid such as a lecithin, a cephalin or an inositide.

The invention may be used in analogy with prior art processes by replacing the phospholipase, e.g. in the production of baked products (WO 0032758, WO 9953769), mayonnaise (GB 1525929, U.S. Pat. No. 4,034,124) or treatment of vegetable oil (U.S. Pat. No. 5,264,367).

Use of Phospholipase

The phospholipase of the invention can be used in various industrial application of phospholipases, e.g. as described below.

Use in Baking

The phospholipase of the invention can be used in the preparation of dough, bread and cakes, e.g. to improve the elasticity of the bread or cake. Thus, the phospholipase can be used in a process for making bread, comprising adding the phospholipase to the ingredients of a dough, kneading the dough and baking the dough to make the bread. This can be done in analogy with U.S. Pat. No. 4,567,056 or WO 99/53769.

Use in Detergent

The variant may be used as a detergent additive, e.g. at a concentration (expressed as pure enzyme protein) of 0.001–10 (e.g. 0.01–1) mg per gram of detergent or 0.001–100 (e.g. 0.01–10) mg per liter of wash liquor.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations. In a laundry detergent, the variant may be effective for the removal of fatty stains, for whiteness maintenance and for dingy cleanup. A laundry detergent composition may be formulated as described in GB 2247025, WO 9901531 or WO 9903962.

The detergent composition of the invention may particularly be formulated for hand or machine dishwashing operations. e.g. as described in GB 2,247,025 (Unilever) or WO 99/01531 (Procter & Gamble). In a dishwashing composition, the variant may be effective for removal of greasy/oily stains, for prevention of the staining/discoloration of the dishware and plastic components of the dishwasher by highly colored components and the avoidance of lime soap deposits on the dishware.

Other Uses

The phospholipase of the invention can be used to improve the filterability of an aqueous solution or slurry of carbohydrate origin by treating it with the phospholipase. This is particularly applicable to a solution of slurry containing a starch hydrolyzate, especially a wheat starch hydrolyzate, since this tends to be difficult to filter and to give cloudy filtrates. The treatment can be done in analogy with EP 219,269 (CPC International).

Further, the phospholipase of the invention may be used for partial hydrolysis of phospholipids, preferably lecithin, to obtain improved phospholipid emulsifiers. This application is further described in Ullmann's Encyclopedia of Industrial Chemistry (Publisher: VCH Weinheim (1996)), JP patent 2794574, and JP-B 6-087751.

Further, the phospholipase of the invention may be used in a process for the production of an animal feed which comprises mixing the phospholipase with feed substances and at least one phospholipid. This can be done in analogy with EP 743 017.

Even further the phospholipase of the invention can be used in a process for reducing the content of phospholipid in an edible oil, comprising treating the oil with the phospholipase so as to hydrolyze a major part of the phospholipid, and separating an aqueous phase containing the hydrolyzed phospholipid from the oil. This process is applicable to the purification of any edible oil which contains phospholipid, e.g. vegetable oil such as soy bean oil, rape seed oil and sunflower oil. The phospholipase may e.g. be used in the processes described in JP-A 2-153997 and U.S. Pat. No. 5,264,367.

Method for Producing Cheese

The phospholipase of the invention may be used for producing cheese in analogy with the process given in U.S. Pat. No. 6,399,121.

In a preferred embodiment of the invention cheese is produced by contacting cheese milk or a fraction of cheese milk with a phospholipase of the invention and producing cheese from the cheese milk.

In a further preferred embodiment cheese is produced by contacting cheese milk or a fraction of cheese milk with a phospholipase, wherein the phospholipase comprises:

a) the sequence given by amino acids 146–153 of SEQ ID NO: 1, amino acids 87–94 of SEQ ID NO: 3, or amino acids 79–86 of SEQ ID NO: 12; or a sequence identical to any of these amino acid sequences except for the substitution of a single amino acid with another amino acid; and b) two cysteine residues located on the N-terminal side of the sequence given in a); and c) two cysteine residues located on the C-terminal side of the sequence given in a).

In the present context the term cheese milk is meant to cover any milk based composition used for production of cheese. A fraction of the cheese milk may be any fraction of the cheese milk such as e.g. cream, skim milk, milk, butter milk, butter or milk fat.

In a preferred embodiment cheese milk or a fraction of cheese milk is contacted with a phospholipase of the invention in an amount sufficient to decrease the oiling-off effect in cheese and/or to increase cheese yield. The oiling-off effect is the tendency of the cheese to form free oil upon storage and/or melting.

In one aspect the invention relates to a process for producing cheese comprising treating a dairy composition with a phospholipase of the invention and producing cheese from the dairy composition.

Another aspect of the invention relates to a process for producing cheese comprising treating a dairy composition with phospholipase and producing cheese from the dairy composition, wherein the phospholipase is selected from the group of fungal/bacterial group XIII PLA2 phospholipases. In a preferred embodiment of the invention the fungal/bacterial group XIII PLA2 is from a fungus, more preferably from a fungus belonging to the *Ascomycetes.*

A phospholipase belonging to the fungal/bacterial group XIII PLA2 may be any phospholipase belonging to this group as defined by Soragni et al., The EMBO Journal, 20 (2001), 5079–5090, and may e.g. be from the species *Tuber*, e.g. *T. borchii, Streptomyces*, e.g. *S. coelicor, Verticillium*, e.g. *V. dahliae, Aspergillus*, e.g. *A. oryzae, Neurospora*, e.g. *N. crassa*, or *Helicosporum.*

A dairy composition according to the invention may be any composition comprising milk constituents. Milk constituents may be any constituent of milk such as milk fat, milk protein, casein, whey protein, and lactose. A milk fraction may be any fraction of milk such as e.g. skim milk, butter milk, whey, cream, milk powder, whole milk powder, skim milk powder. In a preferred embodiment of the invention the dairy composition comprises milk, skim milk, butter milk, whole milk, whey, cream, or any combination thereof. In a more preferred embodiment the dairy composition consists of milk, such as skim milk, whole milk, cream, buttermilk, or any combination thereof.

The enzymatic treatment in the process of the invention may be conducted by dispersing the phospholipase into the dairy composition, and allowing the enzyme reaction to take place at an appropriate holding-time at an appropriate temperature. The treatment with phospholipase may be carried out at conditions chosen to suit the selected enzyme(s) according to principles well known in the art.

The enzymatic treatment may be conducted at any suitable pH, such as e.g., in the range 2–10, such as, at a pH of 4–9 or 5–7. In one embodiment the phospholipase treatment is conducted at 3–60° C., such as at 25–45° C. (e.g., for at least 5 minutes, such as, e.g., for at least 10 minutes or at least 30 minutes, e.g., for 5–120 minutes). The phospholipase is added in a suitable amount to produce the cheese having the desired properties. Preferably, the phospholipase is added in an amount effective to decrease the oiling-off effect in cheese and/or to increase cheese yield. A suitable dosage of phospholipase will usually be in the range 0.001–0.5 mg enzyme protein per g milk fat, preferably 0.01–0.3 mg enzyme protein per g milk fat, more preferably, 0.02–0.1 mg enzyme protein per g milk fat The cheeses produced by the process of the present invention comprise all varieties of cheese, such as, e.g. Campesino, Chester, Danbo, Drabant, Herregard, Manchego, Provolone, Saint Paulin, Soft cheese, Svecia, Taleggio, White cheese, including rennet-curd cheese produced by rennet-coagulation of the cheese curd; ripened cheeses such as Cheddar, Colby, Edam, Muenster, Gruyere, Emmenthal, Camembert, Parmesan and Romano; blue cheese, such as Danish blue cheese; fresh cheeses such as Feta; acid coagulated cheeses such as cream cheese, Neufchatel, Quarg, Cottage Cheese and Queso Blanco. In a preferred embodiment the invention relates to a process for producing pasta filata cheese, such as e.g. Mozzarella and Pizza cheese. Pasta filata, or stretched curd, cheeses are normally distinguished by a unique plasticizing and kneading treatment of the fresh curd in hot water, which imparts the finished cheese its characteristic fibrous structure and melting and stretching properties, cf. e.g. "Mozzarella and Pizza cheese" by Paul S. Kindstedt, Cheese: Chemistry, physics and microbiology, Volume 2: Major Cheese groups, second edition, page 337–341, Chapman & Hall.

Sequence Listing and Deposited Microorganisms

The present application contains information in the form of a sequence listing, which is appended to the application and also submitted on a data carrier accompanying this application. In addition, the present application refers to deposited microorganisms. The contents of the data carrier and the deposited microorganisms are fully incorporated herein by reference.

Deposit of Biological Material

The following biological material has been deposited under the terms of the Budapest Treaty with the Deutsche Sammlung von Mikroorganismen und Zellkulturen GmbH, Mascheroder Weg 1 B, D-38124 Braunschweig, Germany, and given the following accession number:

| Deposit | Accession Number | Date of Deposit |
|---|---|---|
| *E. coli* | DSM 15441 | Feb. 12, 2003 |
| *E. coli* | DSM 15442 | Feb. 12, 2003 |

Materials and Methods

Media and Substrates

Medium YP+2% G
- 10 g yeast extract
- 20 g peptone
- water to 1 L
- autoclave at 121° C., 20 minutes
- add 100 ml 20% sterile glucose solution RA Sporulation Medium:
- 50 g succinic acid
- 12.1 g sodium nitrate
- 1 g glucose
- 20 ml 50× Vogel's salts (Davis, R. H. and F. J. de Serres (1970), Meth. Enzymol. 17A: 79–143)
- components are blended in one liter distilled water and filter sterilized Britton Robinson Buffer
- 0.023 M phosphoric acid
- 0.023 M acetic acid
- 0.023 M boric acid
- Titrated with NaOH or HCl to desired pH Methods Phospholipase Activity (LEU)

Lecithin is hydrolyzed under constant pH and temperature, and the phospholipase activity is determined as the rate of titrant (0.1N NaOH) consumption during neutralization of the liberated fatty acid.

The substrate is soy lecithin (L-α-Phosphotidyl-Choline), and the conditions are pH 8.00, 40.0° C., reaction time 2 min. The unit is defined relative to a standard.

EXAMPLES

Example 1

Expression of a Phospholipase A2 from *Tuber albidum* in *Aspergillus oryzae*

The DNA sequence disclosed in Soragni et al. (supra) was used to design primers for PCR amplification of TbSP1 from genomic DNA, with appropriate restriction sites added to the primer ends to facilitate cloning of the PCR product (SEQ ID NO: 13 and 14). A *Tuber albidum* strain, CBS 272.72, was obtained from the CBS (Centraalbureau voor Schimmelcultures, Utecht, The Netherlands), and cultured on X-agar at 20° C., as recommended by the CBS in List of Cultures, 1996. Mycelium was removed from the surface of the plate, and total DNA was isolated using a FastDNA Spin Kit (BIO101, Inc., Vista, Calif.), following the manufacturer's instrucions. PCR amplification was performed using Extensor Hi-Fidelity PCR Master Mix (ABgene, Surrey, U.K.) following the manufacturers instructions and using an annealing temperature of 52° C. for the first 5 cycles and 62° C. for the last 25 cycles. A single PCR product was obtained, and the sequence was determined and is presented as SEQ ID 9 excluding the added synthetic restriction sites. Comparison of this genomic sequence to the cDNA sequence presented by E. Soragni et al. revealed a single intron. When the intron is removed, the nucleotide sequence rom *T. albidum* CBS272.72 is 92.5% identical to that from *T. borchii* ATCC 96540, the strain used by E. Soragni et al. The corresponding peptide predicted from the *T. albidum* CBS272.72 gene sequence is 93.8% identical to the peptide sequence reported by Soragni et al.

The PCR fragment was restricted with BamHI and XhoI and cloned into the *Aspergillus* expression vector pMStr57 using standard techniques. The expression vector pMStr57 contains the same elements as pCaHj483 (WO 98/00529), with minor modifications made to the *Aspergillus* NA2 promoter, and has sequences for selection and propogation in *E. coli*, and selection and expression in *Aspergillus*.

Specifically, selection in *Aspergillus* is facilitated by the amdS gene of *Aspergillus nidulans*, which allows the use of acetamide as a sole nitrogen source. Expression in *Aspergillus* is mediated by a modified neutral amylase II (NA2) promoter from *Aspergillus niger* which is fused to the 5' leader sequence of the triose phosphate isomerase (tpi) encoding-gene from *Aspergillus nidulans*, and the terminator from the amyloglucosidase-encoding gene from *Aspergillus niger*. The phospholipase A2-encoding gene of the resulting *Aspergillus* expression construct, pMStr70, was sequenced and the sequence was compared to that determined previously for the uncloned PCR fragment, SEQ ID 9. A single T to C mutation was found 52 bp downstream of the stop codon.

*Aspergillus oryzae* was transformed with pMStr70 using standard techniques describeed in Christensen, T. et al., (1988), Biotechnology 6, 1419–1422. Transformants were cultured in YP+2% G medium shaken at 275 RPM at 30° C. and expression of the *Tuber* phospholipase A2, TbPLA2, was monitored by SDS-PAGE.

Protein Characterization

SDS-PAGE revealed two bands, with approximate Mw of 25 and 16 kDa. The supernatant was purified by ion exchange chromatography on a SP-sepharose column equilibrated with 50 mM Acetate-buffer, and eluted with 1M NaCl pH 5.0. The two proteins eluted in two separate fractions. Protein concentration was determined using Protein Assay ESL from Roche. Activity was determined in the LEU assay.

| | Mw kDa | Concentration mg/ml | Activity LEU/ml | Specific activity LEU/mg |
|---|---|---|---|---|
| Pool 1 | 23-25 | 1.32 | 61 | 46 |
| Pool 2 | 16 | 0.42 | 272 | 648 |

The proteins were subjected to N-terminal sequencing. The N-terminal sequence of pool 1 (23–25 kDa band) was found to correspond to amino acids 32–50 of SEQ ID NO: 10. Blotting of pool 2 (16 kDa band) revealed two bands with N-terminal sequences corresponding to amino acids 86–98 and 91–103, respectively. Mass spectral analysis of the two bands showed masses of 13934 and 14348 Da respectively, matching within 5 Da of values calculated from the sequences of amino acids 86–210 and 91–210 of SEQ ID NO: 10, respectively.

Example 2

Purification Procedure for Two Forms of *T. albidium* PLA2 Expressed in *Aspergillus oryzae*

In most fermentations of the *Aspergillus oryzae* transformant described in Example I that produces the *T. albidum* PLA2, two forms of the enzyme were detected during purification. One form ran at 22–23 kDa in SDS-PAGE and corresponds to the peptide reported by Soragni et al. (supra). Additionally, a new form was detected which ran at 16–17 kDa in SDS-PAGE and which has a high specific activity and a high isoelectric point.

Purification of the 22–23 kDa Peptide

Fermentation supernatant containing phospholipase from *T. albidium* expressed in *A. oryzae* (prepared in Example 1) was sterile filtered using EKS filter purchased from Seitz Schenk Bad Kreuznach, Bettringerstrasse 42, Germany D-73550, Waldstetten.

The sterile filtered supernatant was then adjusted to pH of 8 and ionic strength under 4 mSi.

Anion Exchange Chromatography

First step of purification was carried out on anion exchange chromatography using 50 ml Fast flow Q™ sepharose column purchased from Amersham Pharmacia. The column was prequilibrated with 50 mM Tris acetate buffer pH 8. The sterile filtered fermentation broth was then applied on the column and the column was washed with the same buffer until all unbound material was washed out.

Bound proteins were eluted with the same buffer containing 1 M Sodium chloride pH 8 with flow rate of 5 ml/minute and to a final volume of 500 ml total buffer. Fractions of 5 ml each were collected using fraction collector and Phospholipase activity of all fractions containing was assayed qualitatively using Lecithin as substrate using L-α-Phosphatidyl choline purchased from Sigma product P-5638 and activity was assayed using NEFA C kit purchased from Wako Chemicals GmbH, Nissan Strasse 2, 41468 Neuss, Germany. Exact assay is described below.

Substrate solutions containing 10 mg/ml of Lecithin substrate were prepared in different buffers such as 50 mM Acetate pH 5 or 50 mM Hepes pH 7 or 50 mM Tris acetate pH 9 as buffers containing 2 mM CaCl2 and 0.1% Triton X-100 purchased from Fluka chemicals. Substrate was then emulsified by stirring and warming at 50° C. and then cooling to 40° C. and used as substrate.

Assay of activity was carried out using 300 μl of the substrate emulsion incubated with 25 μl of the enzyme fractions for 20 minutes at 40° C. then 30 μl of the assay mixture was transferred to 300 μl of the NEFA C color reagent A prepared as described by the manufacturer and incubated for 10 minutes at 37° C. and 600 μl of the color reagent NEFA C B solution was added to the mixture and further incubated for 10 minutes. The blue color formed was then measured in a spectrophotometer at 505 nm.

Protein Characterization

Fractions containing activity were then pooled and characterized for the molecular weight using SDS-PAGE electrophoresis using Novex Pre casted gels 4 to 20% Tris-Glycine gels purchased from Invitrogen Life Technologies, Carlsbad Calif. 92008, USA.

22–23 kDa protein was detected and blotted and N-terminal analysis was carried out using an Applied Biosystem sequenator.

The first 19 amino acid residues from N-terminal were determined and found to have the sequence of amino acids 32–50 of SEQ ID NO: 10.

Purification of the the 16–17 kDa Peptide

Sterile filtered fermentation supernatant of the *T. albidum* phospholiplase expressed in *A. oryzae* was adjusted to pH 4.7 and ionic strength was adjusted below 4 mSi.

Cation Exchange Chromatography

SP-sepharose™ fast flow was purchased from Amersham Pharmacia. 50 ml Column was packed and equilibrated with 50 mM acetate buffer pH 4.7 the fermentation supernatant was then applied on column and unbound material was washed using the same buffer.

Bound protein with high pI was then eluted with a linear salt gradient using 50 mM acetate buffer pH 4.7 containing 1 M Sodium chloride. Fractions and flow rate were similar to those used for the low pI form of the phospholipase. Phospholipase activity in the fractions was assayed qualitatively using NEFA kit as above. Fractions containing Phospholipase activity were pooled and SDS-PAGE was carried out as described above.

16–17 kDa protein was observed which had a high isoelectric point, above 9.

The N-terminal analysis of the protein was carried out after blotting the protein and using Applied biosystem sequentaor which showed an N-terminal which was completely different from the one published in Soragni et al. (supra). Thus, the *T. albidum* PLA2 was found to have two forms deriving from differential N-terminal processing with N-terminal sequences corresponding to amino acids 86–105 and 91–110 of SEQ ID NO: 10, respectively.

Example 3

Cheese Making with *T. albidum* Phospholipase

Pasteurized, non-homogenized cream (North Carolina State University Dairy Plant) was used to standardize five hundred grams pasteurized, non-homogenized skim milk (North Carolina State University Dairy Plant) to 3.5% fat thus producing full fat mozzarella cheese.

The cheese milk for each experiment was treated with either the 16–17 kD *T. albidum* phospholipase prepared according to example 2, or the commercial phospholipase Lecitase® 10L (Novozymes A/S, Bagsvaerd, Denmark), and placed in a 35° C. water bath until equilibrated to that temperature. The initial pH of the cheese milk was taken and 0.01% (w/w) of starter culture was added.

pH was monitored until a pH of 6.4 was reached. 250 pl rennet (Novozym 89L) was diluted to in 9 ml total solution with deionised water, one ml of this solution was added to the cheese milk and the cheese milk was stirred vigorously for 3 minutes. The stir bar was removed and the rennetted milk was allowed to sit at 35° C.

After the above treatments, curd was ready to cut when a spatula was inserted and sharp edges were seen. The cheese was cut by pushing the cutter down and while holding the beaker quickly turning the cutter and finally pulling the cutter up. The curd was allowed to rest 5 minutes then stirred gently with spoon. Temperature was raised to 41° C. with intermittent gentle agitation for ~45 min or until the pH dropped to 6.0–5.9. The curd was drained using cheesecloth then replaced in the beaker and kept at 41° C. in water bath while pouring off whey as needed.

When the curd reached pH 5.3, the stainless steel bowl with the curd in it was flooded in a water bath at 69° C. for 5 minutes then hand stretched. Curd was tempered in cold icewater for 30 minutes. The cheese curd was dried out with paper towel, weighed and refrigerated overnight.

Control cheese making experiments were made from the same batch of milk following the same procedures except that no phospholipase was added.

Actual cheese yield was calculated as the weight of cheese after stretching relative to the total weight of cheese milk.

Moisture adjusted cheese yield was expressed as the actual yield adjusted to standard constant level of moisture. Moisture adjusted yield was calculated by multiplying the actual yield and the ratio of actual moisture content to standard moisture, according to the following formula:

$$Y_{adj}=(Y_{act}\times 1-M_{act})/(1-M_{std})$$

where $Y_{adj}$=moisture adjusted cheese yield, $Y_{act}$=actual cheese yield, $M_{act}$=actual moisture fraction & $M_{std}$=standard moisture fraction (0.48).

The moisture adjusted cheese yield of all experiments and controls are shown in table 1

TABLE 1

| Treatment | Phospholipase mg enzyme protein/g fat | Moisture adjusted cheese yield | Yield increase compared to control |
|---|---|---|---|
| Control | 0 | 10.72 | |
| *T. albidum* PLA2 | 0.055 | 11.04 | 2.9% |
| Control | 0 | 11.25 | |
| *T. albidum* PLA2 | 0.055 | 11.57 | 2.8% |
| Control | 0 | 9.22 | |
| Lecitase ® 10L | 0.18 | 9.48 | 2.7% |
| Control | 0 | 9.62 | |
| Lecitase ® 10L | 0.18 | 9.90 | 2.8% |

Example 4

Cloning and Expression of a Phospholipase (FvPLA2) from *Fusarium venenatum* in *Aspergillus oryzae*

Cells of the *Fusarium venenatum* A3/5 (originally deposited as *Fusarium graminearum* ATCC 20334 and recently reclassified as *Fusarium venenatum* by Yoder and Christianson, 1998, Fungal Genetics and Biology 23: 62–80; and O'Donnell et al., 1998, Fungal Genetics and Biology 23: 57–67) were grown for two days in Vogel's minimal medium (Davis, R. H. and F. J. de Serres (1970), Meth. Enzymol. 17A:79–143) at 28° C. in shaking culture, filtered on sterile Miracloth (Calbiochem, San Diego, Calif., USA), and transferred to "RA sporulation medium" in which they were incubated in shaking culture for an additional 24 hr at 28° C. Cells and spores were collected by centrifugation and lysed, and RNA was extracted and transcribed into cDNA that was cloned into pZErO-2 by the methods described in WO 00/56762. The number of independent clones in this library before amplification was 2.5×105, of which 92% contained inserts ranging in size from 550–2500 bp. Partial DNA sequences were determined for approximately 1000 randomly chosen clones and the sequences were stored in a computer database by methods described in WO 00/56762.

The nucleotide sequence of a cDNA encoding TbSP1, a phospholipase A2 from *Tuber borchii*, and the corresponding peptide translation were reported by E. Soragni et al., 2001. This translated peptide sequence was compared to translations of the *Fusarium venenatum* partial cDNA sequences using the TFASTXY program, version 3.3t08 (Pearson et al., 1997). One translated *F. venenatum* sequence was identified as having 42% identity to TbSP1 through a 125 amino acid overlap. The complete sequence of the cDNA insert of the corresponding clone, FM0700, was determined and is presented as SEQ ID NO: 15, and the peptide translated from this sequence, FvPLA2, is presented as SEQ ID NO: 16. This sequence was used to design the primers FvPLA1 and FvPLA2.2 for PCR amplification of the FvPLA2 encoding-gene from FM0700, with appropriate restriction sites added to the primer ends to facilitate sub-cloning of the PCR product.

```
FvPLA1:      CTGGGATCCTCAAGATGAAGTTCAGCG

FvPLA2.2:     GACCTCGAGACCCGCCATTTAAGATT
```

PCR amplification was performed using Extensor Hi-Fidelity PCR Master Mix (ABgene, Surrey, U.K.) following the manufacturers instructions and using an annealing temperature of 52° C. and an extension temperature of 60° C. for 20 cycles.

The PCR fragment was restricted with BamHI and XhoI and cloned into the *Aspergillus* expression vector pMStr57 using standard techniques. The expression vector pMStr57 contains the same elements as pCaHj483 (WO 98/00529), with minor modifications made to the *Aspergillus* NA2 promoter as described for the vector pMT2188 in WO 01/12794, and has sequences for selection and propagation in *E. coli*, and selection and expression in *Aspergillus*. Specifically, selection in *Aspergillus* is facilitated by the amdS gene of *Aspergillus nidulans*, which allows the use of acetamide as a sole nitrogen source. Expression in *Aspergillus* is mediated by a modified neutral amylase II (NA2) promoter from *Aspergillus niger* which is fused to the 5' leader sequence of the triose phosphate isomerase (tpi) encoding-gene from *Aspergillus nidulans*, and the terminator from the amyloglucosidase-encoding gene from *Aspergillus niger*. The phospholipase-encoding gene of the resulting *Aspergillus* expression construct, pMStr77, was sequenced and the sequence agreed completely with that determined previously for the insert of FM0700.

The *Aspergillus oryzae* strain BECh2 (WO 00/39322) was transformed with pMStr77 using standard techniques (T. Christensen et al., 1988). Transformants were cultured in YP+2% G medium shaken at 275 RPM at 30° C. and expression of FvPLA2 was monitored by SDS-PAGE.

A strain of *Eschericia coli* containing a gene encoding the phospholipase from *F. venenatum* was deposited by the inventors under the terms of the Budapest Treaty with Deutsche Sammlung von Microorganismen und Zellkulturen GmbH, Mascheroder Weg 1b, D-38124 Braunschweig, Germany. The deposit date was 12 Feb. 2003, and the accession number was DSM 15442.

Example 5

Purification and Sequence Comparison of FvPLA2

FvPLA2 from the fermentation of example 4 was purified by ion exchange chromatography on a SP-sepharose column equilibrated with 50 mM Acetate-buffer pH 4.7, and eluted with 1M NaCl pH 4.7. Fractions were analyzed on SDS-PAGE, and fractions containing a 14 kDa protein were pooled. The identity of the pure protein was confirmed by determining the the N-terminal sequence, which was identical to the sequence from amino acid (aa) 29–40 of SEQ ID NO: 16. Additionally, the mass of the peptide was determined by mass spectral analysis, because the apparent size estimated from SDS-PAGE, 14 kDa, is smaller than that of the peptide predicted by processing the theoretical peptide in SEQ ID NO: 16. The mass of the purified, active FvPLA2 was found to be 13336 Da. This molecular mass indicates additional processing at the C-terminus, and is consistent with a cleavage between amino acids 149 and 150 in SEQ ID NO: 16, as the peptide sequence from amino acid 29 to 149 has a theoretical mass of 13335,66 Da.

A comparison of the mature processed peptide (amino acids 29–149 of SEQ ID NO: 16) with known sequences showed that the closest prior-art sequence was a phospholipase from *Verticillium dahliae* translated from Unisequence ID: VD0100C34 from the COGEME Phytopathogenic Fungi and Oomycete EST Database Version 1.2 (http://cogeme.ex.ac.uk/) (Soanes et al. (2002) Genomics of phytopathogenic fungi and the development of bioinformatic resources. Mol Plant Microbe Interact. 15(5):421–7). The processing of the partial peptide predicted from the *V. dahliae* sequence was estimated by comparison to the found processing for FvPLA2. The identity between amino acids 29 to 149 of SEQ ID NO: 16 and the estimated sequence of the mature peptide of the *V. dahliae* phospholipase was calculated to be 77%.

Example 6

Physical Properties of FvPLA2

Catalytic Activity

Phospholipase activity as a function of enzyme concentration was determined in the LEU assay for FvPLA2 of example 4. Results are shown in table 1.

TABLE 1

| Enzyme conc. (μg/ml) | LEU (μeq NaOH/min) |
|---|---|
| 71.1 | 14.0 |
| 53.3 | 12.7 |
| 21.3 | 10.6 |
| 10.7 | 7.4 |
| 5.3 | 5.6 |
| 2.7 | 4.1 |

Temperature Profile

The enzyme activity as a function of temperature was determined for an enzyme solution with a concentration of 5.3 μg/ml. Other conditions as in the LEU assay. Results are shown in table 2.

TABLE 2

| Temperature (° C.) | LEU (μeq NaOH/min) |
|---|---|
| 25 | 3.10 |
| 35 | 4.87 |
| 40 | 5.41 |
| 45 | 6.97 |
| 50 | 7.86 |
| 55 | 9.03 |
| 60 | 8.27 |
| 65 | 6.90 |

pH Stability

The enzyme was diluted in a Britton Robinson buffer at the specified pH for 30 min at 30° C. After further dilution in water catalytic activity was measured in the LEU assay. Results are shown in table 3.

TABLE 3

| pH | LEU (μeq NaOH/min) |
|---|---|
| 2 | 3.78 |
| 3 | 5.11 |
| 4 | 5.60 |
| 5 | 5.49 |
| 6 | 5.37 |
| 7 | 5.61 |
| 8 | 5.52 |
| 9 | 5.64 |
| 10 | 5.50 |
| 11 | 5.21 |

Thermo Stability

The enzyme was diluted in Britton Robinson buffer at pH 3 and 10 respectively, and at pH 7 with 30% sorbitol. After incubation at the specified temperature for 30 minutes, the solution was cooled to the reaction temperature and assayed in the LEU assay. The results are shown in table 4; activities are given relative to the highest measured activity.

TABLE 4

Relative activity (%) as a function of pH and temperature

| Temperature (° C.) | pH 3 | pH 10 | pH7/30% sorbitol |
|---|---|---|---|
| 30 | 100% | 100% | 87% |
| 40 | 95% | 92% | 100% |
| 50 | 16% | 14% | 68% |
| 60 | 1% | 0% | 2% |

Example 7

Cheese Making with FvPLA2

Pasteurized, non-homogenized cream (North Carolina State University Dairy Plant) was used to standardize five hundred grams pasteurized, non-homogenized skim milk (North Carolina State University Dairy Plant) to 3.5% fat thus producing full fat mozzarella cheese.

The cheese milk for each experiment was treated with either the *F. venenatum* phospholipase (FvPLA2) prepared according to example 5, or of the commercial phospholipase Lecitase® 10L (Novozymes A/S, Bagsvaerd, Denmark), and placed in a 35° C. water bath until equilibrated to that temperature. The initial pH of the cheese milk was taken and 0.01% (w/w) of starter culture at was added.

pH was monitored until a pH of 6.4 was reached. 250 µl rennet (Novozym 89L) was diluted to in 9 ml total solution with deionized water, one ml of this solution was added to the cheese milk and the cheese milk was stirred vigorously for 3 minutes. The stir bar was removed and the rennetted milk was allowed to sit at 35° C.

After the above treatments, curd was ready to cut when a spatula was inserted and sharp edges were seen. The cheese was cut by pushing the cutter down and while holding the beaker quickly turning the cutter and finally pulling the cutter up. The curd was allowed to rest 5 minutes then stirred gently with spoon. Temperature was raised to 41° C. with intermittent gentle agitation for ~45 min or until the pH dropped to 6.0–5.9. The curd was drained using cheese-cloth then replaced in the beaker and kept at 41° C. in water bath while pouring off whey as needed.

When the curd reached pH 5.3, the stainless steel bowl with the curd in it was flooded in a water bath at 69° C. for 5 minutes then hand stretched. Curd was tempered in cold icewater for 30 minutes. The cheese curd was dried out with paper towel, weighed and refrigerated overnight.

Control cheese making experiments were made from the same batch of milk following the same procedures except that no phospholipase was added.

Actual cheese yield was calculated as the weight of cheese after stretching relative to the total weight of cheese milk.

Moisture adjusted cheese yield was expressed as the actual yield adjusted to standard constant level of moisture. Moisture adjusted yield was calculated by multiplying the actual yield and the ratio of actual moisture content to standard moisture, according to the following formula:

$$Y\text{adj}=Y\text{act}\times(1-M\text{act})/(1-M\text{std})$$

where Yadj=moisture adjusted cheese yield, Yact=actual cheese yield, Mact=actual moisture fraction & Mstd=standard moisture fraction (0.48).

The moisture adjusted cheese yield of all experiments and controls are shown in table 5.

TABLE 5

| Treatment | Phospholipase mg enzyme protein/g fat | Moisture adjusted cheese yield | Yield increase compared to control |
|---|---|---|---|
| Control | 0 | 11.70 | |
| FvPLA2 | 0.071 | 11.95 | 2.1% |
| Control | 0 | 11.50 | |
| FvPLA2 | 0.071 | 11.83 | 2.8% |
| Control | 0 | 9.22 | |
| Lecitase ® 10L | 0.18 | 9.48 | 2.7% |
| Control | 0 | 9.62 | |
| Lecitase ® 10L | 0.18 | 9.90 | 2.8% |

Example 8

Cheese Making with FvPLA2

Milk was pasteurized at 72° C. for 15 seconds and then cooled to below 10° C. Milk was standardized to 2.4% fat with cream. After standardization the milk was preheated in a heat exchanger at a pre-ripening temperature of 34.5° C. 150 kg milk was poured into each cheese vat and 15 g culture (F-DVS ST-M6) was added. The phospholipase from example 5 was added in a dosage of 5 LEU/g fat and the milk was incubated for 1 h at 34.5° C. Rennet (Chy-Max Plus, 200 IMCU) was added and agitation was continued for not more than 4 min.

After approx. 60 min when the coagulum was judged ready it was cut using 10 mm knives. The agitator was returned to the vat and after 10 min. the scalding was started by increasing the temperature to 41° C. within 30 min. After reaching 41° C. a further stirring for approximately 20 min. took place until a titratable acidity of 0.15–0.16% was reached. The curd was allowed to settle in the vat, and whey was drained. The curd was cut in uniform blocks and the blocks were turned and stacked into two. Subsequently, at intervals of 10 min. the blocks were turned and kept in stacks of two. At a pH of around 5.15–5.20, the curd was milled in a milling machine. The curd pieces were added two percent of salt (weight/weight).

After milling all the curd was added into the stretcher, which contains 70 l preheated water at 74° C. Around 20 l of hot water was transferred to the upper chamber and the cheese is added. When the curd temperature reached 62° C., the stretching was stopped and the curd moved to the extruder. Cheeses were extruded into 8–9 cheese loaves, each of 2.3 kg, and cooled in 5–7° C. water for 20 min. After 20 min. cooling the cheeses were moved to the saturated brine and brined for 1.5 hours at 5–6° C. The brine was made by blending 120 kg water, adding salt to 22Be, 750 g CaCl2 (34% solution) and adjusted to pH 5.1. After brining each cheese was dried for around 30 min. and weighed before vacuum packaging. Samples were taken for pH and compositional analyses (moisture, salt, fat and protein) after about 1 week's storage in cold room.

Actual yield (AY) was adjusted to 48% moisture in cheese:

$$\text{Adj Yield} = \frac{AY \times (100 - \%\ \text{moisture})}{100 - 48}$$

TABLE 6

| | Adjusted yield (kg) Control | Adjusted yield (kg) Experimental | Average yield increase (kg) | Yield increase (%) |
|---|---|---|---|---|
| Day 1 | 10.62 | 10.81 | | |
| | 10.70 | 10.90 | 0.195 | 1.8 |
| Day 2 | 9.90 | 10.16 | | |
| | 9.95 | 10.14 | 0.225 | 2.3 |
| Day 3 | 10.00 | 10.15 | | |
| | 10.01 | 10.16 | 0.15 | 1.5 |

Example 9

Over-expression of *Aspergillus oryzae* PLA2 (AoPLA2) in *Aspergillus oryzae*

Medium

DAP2C-1

11 g $MgSO_4.7H_2O$
1 g $KH_2PO_4$
2 g Citric acid, monohydrate
30 g maltodextrin
6 g $K_3PO_4.3H_2O$
0.5 g yeast extract
0.5 ml trace metals solution
1 ml Pluronic PE 6100 (BASF, Ludwigshafen, Germany)

Components are blended in one liter distilled water and portioned out to flasks, adding 250 mg CaCO3 to each 150 ml portion.

The medium is sterilized in an autoclave. After cooling the following is added to 1 liter of medium:

23 ml 50% w/v $(NH_4)_2HPO_4$, filter sterilized
33 ml 20% lactic acid, filter sterilized Trace Metals Solution 6.8 g $ZnCl_2$
2.5 g $CuSO_4.5H_2O$
0.24 g $NiCl_2.6H_2O$
13.9 g $FeSO_4.7H_2O$
8.45 g $MnSO_4.H_2O$
3 g Citric acid, monohydrate Components are blended in one liter distilled water.

The cloning and partial sequencing of a cDNA encoding a phospholipase A2 from *Aspergillus oryzae* is described in WO 00/56762. The full sequence of the clone, AS3812, is given in SEQ ID NO: 6.

This sequence was used to design the primer AoPLA1 for use with the vector primer pYESrev in PCR amplification of the PLA2 encoding-gene from AS3812 with the addition of a restriction site to facilitate sub-cloning of the PCR product:

AoPLA1: TGAGGATCCATCATGAAGAACATCTTCG
pYESrev: gggcgtgaatgtaagcgtgac

PCR amplification was accomplished using Extensor Hi-Fidelity PCR Master Mix (AB-gene, Surrey, U.K.) following the manufacturers instructions and using an annealing temperature of 52° C. for the first 5 cycles and 62° C. for the last 25 cycles, and an extension time of 1.5 minutes.

The PCR fragment was restricted with BamHI and XhoI and cloned into the *Aspergillus* expression vector pMStr57 (described in Example 1) using standard techniques. The phospholipase-encoding gene of the resulting *Aspergillus* expression construct, pMStr71, was sequenced and the sequence agreed completely with that determined previously for the insert of AS3812.

The *Aspergillus oryzae* strain BECh2 (WO 00/39322) was transformed with pMStr71 using standard techniques (T. Christensen et al., 1988). Transformants were cultured in DAP2C-1 medium shaken at 270 RPM at 37° C. for 4 days and expression of phospholipase was monitored by SDS-PAGE.

Example 10

Purification and Determination of Peptide Processing

The *Aspergillus oryzae* phospholipase from the fermentation of example 9 was filtered through 0.22μ sterile filter Seitz-EKS obtained from Pall Corporation (Pall SeitzSchenk Filter Systems GmbH Pianiger Str.137 D-55543 Bad Kreuznach, Germany). The sterile filtered solution was then adjusted to pH 4.7 using dilute acetic acid. Ionic strength of the fermentation supernatant was then adjusted so that salt concentration was low and ionic strength was under 4 mSi. Purification of the desired PLA2 protein was obtained by cation exchange chromatography using SP sepharose fast Flow matrix obtained from Amersham-Pharmacia (Sweden). The cation exchanger matrix was packed washed and pre-equilibrated with 50 mM Sodium acetate buffer pH 4.7 (Buffer A) on XK26 column obtained from Amersham Pharmacia. Fermentation supernatant containing the desired PLA2 adjusted for pH and ionic strength was then applied on the column. Unbound material was then washed with the buffer A until all the UV absorbing material was washed out, which was monitored by UV detector attached to fraction collector equipment. Bound proteins were then eluted with a linear salt gradient using Buffer B, which contained 1 M Sodium chloride as salt in 50 mM Sodium acetate buffer pH 4.7. Total volume of the linear gradient reaching 1 M salt concentration was around 500 ml (10 column volume). Fractions of 10 ml each were collected during the elution. All the fractions were assayed for phospholipase activity using Lecithin as substrate obtained from Sigma chemicals. Fatty acids released from Lecithin on incubation with the phospholipase were detected using NEFA C kit obtained from Waco chemicals. Fractions containing phospholipase activity were then checked for purity of the protein using standard SDS-PAGE technique. Fractions were pooled that contained a single band of the desired PLA2 showing molecular weight of around 16 kDa, as determined by comparison to molecular weight standards from Amersham-Pharmacia.

The identity of the pure protein was confirmed by determining the N-terminal sequence, which was identical to the sequence from amino acid (aa) 37–45 of SEQ ID NO: 7. Additionally, the mass of the peptide was determined by mass spectral analysis. The purified, active *Aspergillus* PLA2 gave two masses, 14114 and 14242 Da. These molecular masses indicate additional processing at the C-terminus, consistent with cleavage between amino acids 121 and 122 in SEQ ID NO: 7, as the peptide sequence from amino acid 37 to 121 has a theoretical mass of 14114.11 Da and cleavage between amino acids 122 and 123, predicting the peptide sequence from amino acid 37 to 123 with a theoretical mass of 14242.29 Da.

Example 11

Expression of Incompletely Processed Phospholipase from *Aspergillus oryzae* and *Fusarium venenatum*

Processing of the *Aspergillus oryzae* PLA2 (AoPLA2) and the *Fusarium venenatum* PLA (FvPLA2) at both the N- and C-termini occurs at single or multiple basic residues (lys or arg), typical of the cleavage sites of the Kexin-like maturases, which are often responsible for processing propeptides (Jalving, R., et al. (2000) Appl. Environ. Microbiol. 66: 363–368). In order to determine the effect of processing on the activity of AoPLA2 and FvPLA2, the enzymes were expressed in a Kexin deficient strain of *Aspergillus oryzae*. Processing was then assessed by SDS-PAGE, and phospholipase activity was measured for cultures of strains expressing AoPLA2 and FvPLA2 in both wild-type and Kexin deficient backgrounds.

A Kexin deficient strain of *Aspergillus oryzae* ($kexB^-$) was constructed by a disrupting the kexB gene of *A. oryzae* (EMBL:AB056727) by methods established in the art, such as those described in WO 98/12300 and U.S. Pat. No. 6,013,452. Disruption of kexB was confirmed by Southern blot analysis and by monitoring the expression of peptides where KexB is known to be responsible for maturation. The $kexB^-$ strain was transformed with the AoPLA2 expression construct described in Example 9, and with the FvPLA2 expression construct described in Example 4. These strains were fermented in YP+2% G at 30° C., along with the $kexB^+$ expression strains for both AoPLA2 and FvPLA2 described in Examples 9 and 4, and untransformed strains as controls. AoPLA2 expressing strains were shaken at 200 RPM for 4 days while FvPLA2 expressing strains were shaken at 275 RPm for 3 days. Phospholipase expression and processing were assessed by SDS-PAGE.

In SDS-PAGE analysis, AoPLA2 was resolved as a distinct single band in both $kexB^+$ and $kexB^-$ strains. When expressed in the $kexB^+$ strain, AoPLA2 ran at ca. 16 kDa, consistent with the migration observed earlier for fully processed AoPLA2 (Example 10), while in the $kexB^-$ strain, AoPLA2 ran at ca. 27–28 kDa, consistent with a lack of processing or incomplete processing. When expressed in the $kexB^+$ strain FvPLA2 was resolved as two bands with apparent molecular weights of 17 kDa and 14 kDa. The 14 kDa band corresponds to the fully processed peptide (Example 5), while the 17 kDa peptide is a partially processed form. When expressed in the $kexB^-$ strain, FvPLA2 ran as a single band at ca. 18–19 kDa, a size consistent with incomplete processing. No similar bands were seen in any of the control samples from untransformed strains. Relative band intensities suggest that expression of AoPLA2 in the $kexB^-$ strain was 1/5 to 1/10 the level of that in the $kexB^+$ strain, while expression of FvPLA2 in the $kexB^-$ strain was the same to ½ the level of that in the $kexB^+$ strain.

The activity of the phospholipases produced by each strain was determined in the LEU assay and is shown in table 7.

TABLE 7

| Strain genotype | | | |
|---|---|---|---|
| KexB | FvPLA | AoPLA2 | Activity LEU/ml |
| + | – | – | 0 |
| – | – | – | 0 |
| + | + | – | 38 |
| – | + | – | 0 |
| + | – | + | 56 |
| – | – | + | 0 |

The invention claimed is:

1. A method of producing a phospholipase which comprises processing an expressed fungal peptide so as to cleave off a peptide from the C-terminal end and/or a peptide from the N-terminal end to obtain a core peptide with phospholipase activity, wherein the core peptide comprises a) the amino acid sequence given by amino acids 146–153 of SEQ ID NO: 1, amino acids 87–94 of SEQ ID NO: 3, or amino acids 79–86 of SEQ ID NO: 12; or a sequence identical to any of these amino acid sequences except for the substitution of a single amino acid with another amino acid; and b) at least two cysteine residues located on the N-terminal side of the sequence given in a); and c) at least two cysteine residues located on the C-terminal side of the sequence given in a).

2. The method of claim 1 wherein the expressed peptide is expressed in a filamentous fungal host cell transformed with DNA encoding the expressed peptide.

3. The method of claim 2 wherein the host cell is an *Aspergillus, Fusarium* or *Trichoderma*, particularly *A. oryzae, A. niger, F. venenatum* or *T. reesei.*

4. The method of claim 2 wherein the expressed peptide is processed in vivo by the host cell.

5. The method of claim 1 wherein the core peptide has a length of 100–150 amino acids.

6. The method of claim 1 wherein the phospholipase has a specific phospholipase activity which is at least 2 times the activity of the expressed peptide before processing.

7. The method of claim 1 wherein the expressed peptide is derived from *Tuber, Verticillium, Neurospora, Aspergillus*, or *Helicosporum*, particularly *T. borchii, T. albidum, V. dahliae, V. tenerum, N. crassa, A. oryzae*, or *Helicosporium* sp.HN1.

8. The method of claim 1 wherein the expressed peptide is cleaved within 0–18 amino acids on the N-terminal side of the sequence aligning with amino acids 97–101 of SEQ ID NO: 1, when the complete expressed peptide sequence is aligned simultaneously with the sequences given in SEQ ID NO: 1, SEQ ID NO: 3, SEQ ID NO: 4, SEQ ID NO: 5, SEQ ID NO: 7, SEQ ID NO: 8, SEQ ID NO: 10, and SEQ ID NO: 12.

9. The method of claim 1 wherein the expressed peptide is cleaved within 0–11 amino acids on the C-terminal side of the sequence aligning with amino acids 204–209 of SEQ ID NO: 1, when the complete expressed peptide sequence is aligned simultaneously with the sequences given in SEQ ID NO: 1, SEQ ID NO: 3, SEQ ID NO: 4, SEQ ID NO: 5, SEQ ID NO: 7, SEQ ID NO: 8, SEQ ID NO: 10, and SEQ ID NO: 12.

10. The method of claim 1 wherein the expressed peptide is cleaved within 10 amino acids of a Kex2 processing site or within 11 amino acids of an FG sequence or both.

11. A method of hydrolyzing a phospholipid comprising contacting the phospholipid with a phospholipase produced by the method of claim 1.

12. A method of producing cheese comprising contacting cheese milk or a fraction of cheese milk with a phospholipase, wherein the phospholipase comprises:

d) the sequence given by amino acids 146–153 of SEQ ID NO: 1, amino acids 87–94 of SEQ ID NO: 3, or amino acids 79–86 of SEQ ID NO: 12; or a sequence identical to any of these amino acid sequences except for the substitution of a single amino acid with another amino acid; and e) two cysteine residues located on the N-terminal side of the sequence given in a); and f) two cysteine residues located on the C-terminal side of the sequence given in a).

13. A method of producing cheese comprising contacting cheese milk or a fraction of cheese milk with a phospholipase produced by the method of claim 1.

* * * * *

SEQUENCE LISTING

```
<160> NUMBER OF SEQ ID NOS: 16

<210> SEQ ID NO 1
<211> LENGTH: 211
<212> TYPE: PRT
<213> ORGANISM: Tuber borchii

<400> SEQUENCE: 1

Met Val Lys Ile Ala Ala Ile Ile Leu Leu Met Gly Ile Leu Ala Asn
1               5                   10                  15

Ala Ala Ala Ile Pro Val Ser Glu Pro Ala Ala Leu Asn Lys Arg Gly
            20                  25                  30

Asn Ala Glu Val Ile Ala Glu Gln Thr Gly Asp Val Pro Asp Phe Asn
        35                  40                  45

Thr Gln Ile Thr Glu Pro Thr Gly Glu Gly Asp Arg Gly Asp Val Ala
    50                  55                  60

Asp Glu Thr Asn Leu Ser Thr Asp Ile Val Pro Glu Thr Glu Ala Ala
65                  70                  75                  80

Ser Phe Ala Ala Ser Ser Val Ser Ala Ala Leu Ser Pro Val Ser Asp
                85                  90                  95

Thr Asp Arg Leu Leu Tyr Ser Thr Ala Met Pro Ala Phe Leu Thr Ala
            100                 105                 110

Lys Arg Asn Lys Asn Pro Gly Asn Leu Asp Trp Ser Asp Asp Gly Cys
        115                 120                 125

Ser Lys Ser Pro Asp Arg Pro Ala Gly Phe Asn Phe Leu Asp Ser Cys
    130                 135                 140
```

-continued

```
Lys Arg His Asp Phe Gly Tyr Arg Asn Tyr Lys Lys Gln His Arg Phe
145                 150                 155                 160

Thr Glu Ala Asn Arg Lys Arg Ile Asp Asp Asn Phe Lys Lys Asp Leu
                165                 170                 175

Tyr Asn Glu Cys Ala Lys Tyr Ser Gly Leu Glu Ser Trp Lys Gly Val
            180                 185                 190

Ala Cys Arg Lys Ile Ala Asn Thr Tyr Tyr Asp Ala Val Arg Thr Phe
        195                 200                 205

Gly Trp Leu
    210


<210> SEQ ID NO 2
<211> LENGTH: 588
<212> TYPE: DNA
<213> ORGANISM: Verticillium dahliae
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: CDS
<222> LOCATION: (72)..(587)

<400> SEQUENCE: 2

cagtttgaag tcccagcccc tgctnntcct cctgcttctc cccgtccagt ctttgggatt      60

ttcctctcat c atg aag ttc aac gca att ctc ctg gcc ctc gtg cct gcc      110
             Met Lys Phe Asn Ala Ile Leu Leu Ala Leu Val Pro Ala
             1               5                   10

gcc ctg gct ctg ccc acc acc gac gag gcg cag acc ccc aag ctc gcc      158
Ala Leu Ala Leu Pro Thr Thr Asp Glu Ala Gln Thr Pro Lys Leu Ala
    15                  20                  25

gcg cgc cag agc atc acg gcc gtc acc gac agc ctg tcc ttc tcc ctg      206
Ala Arg Gln Ser Ile Thr Ala Val Thr Asp Ser Leu Ser Phe Ser Leu
30                  35                  40                  45

acg ctg cct cag ttc acc acg cgc cgc aac aac cgc aac ccc gcc aac      254
Thr Leu Pro Gln Phe Thr Thr Arg Arg Asn Asn Arg Asn Pro Ala Asn
                50                  55                  60

ctc gac tgg agc tcc gac ggc tgc aca acg tct cct gac aac cca ttc      302
Leu Asp Trp Ser Ser Asp Gly Cys Thr Thr Ser Pro Asp Asn Pro Phe
            65                  70                  75

gga ttc ccc ttt gtg ccg gcc tgc cac cgc cac gac ttt ggc tac cac      350
Gly Phe Pro Phe Val Pro Ala Cys His Arg His Asp Phe Gly Tyr His
        80                  85                  90

aac ttc cgc gcc cag acc cgc ttc acc gag agc aac aag ctc cgc atc      398
Asn Phe Arg Ala Gln Thr Arg Phe Thr Glu Ser Asn Lys Leu Arg Ile
    95                  100                 105

gac aac cag ttc agg acc gat ctg agg ttc cag tgc cag tct tcg agc      446
Asp Asn Gln Phe Arg Thr Asp Leu Arg Phe Gln Cys Gln Ser Ser Ser
110                 115                 120                 125

gtg cgc ggc gtg tgc aac gcc ctg gcg gac gtc tac tac tct gcc gtc      494
Val Arg Gly Val Cys Asn Ala Leu Ala Asp Val Tyr Tyr Ser Ala Val
                130                 135                 140

cgg gcg ttc ggc ggt gac gac gcc acc ccc ggc aag agg gac gag cac      542
Arg Ala Phe Gly Gly Asp Asp Ala Thr Pro Gly Lys Arg Asp Glu His
            145                 150                 155

tcg gaa ctc gtc ggc atc tac gac gag aag gtc ggc atc tac gat a        588
Ser Glu Leu Val Gly Ile Tyr Asp Glu Lys Val Gly Ile Tyr Asp
        160                 165                 170
```

-continued

<210> SEQ ID NO 3
<211> LENGTH: 172
<212> TYPE: PRT
<213> ORGANISM: Verticillium dahliae

<400> SEQUENCE: 3

```
Met Lys Phe Asn Ala Ile Leu Leu Ala Leu Val Pro Ala Ala Leu Ala
1               5                   10                  15

Leu Pro Thr Thr Asp Glu Ala Gln Thr Pro Lys Leu Ala Ala Arg Gln
            20                  25                  30

Ser Ile Thr Ala Val Thr Asp Ser Leu Ser Phe Ser Leu Thr Leu Pro
        35                  40                  45

Gln Phe Thr Thr Arg Arg Asn Asn Arg Asn Pro Ala Asn Leu Asp Trp
    50                  55                  60

Ser Ser Asp Gly Cys Thr Thr Ser Pro Asp Asn Pro Phe Gly Phe Pro
65                  70                  75                  80

Phe Val Pro Ala Cys His Arg His Asp Phe Gly Tyr His Asn Phe Arg
                85                  90                  95

Ala Gln Thr Arg Phe Thr Glu Ser Asn Lys Leu Arg Ile Asp Asn Gln
            100                 105                 110

Phe Arg Thr Asp Leu Arg Phe Gln Cys Gln Ser Ser Ser Val Arg Gly
        115                 120                 125

Val Cys Asn Ala Leu Ala Asp Val Tyr Tyr Ser Ala Val Arg Ala Phe
    130                 135                 140

Gly Gly Asp Asp Ala Thr Pro Gly Lys Arg Asp Glu His Ser Glu Leu
145                 150                 155                 160

Val Gly Ile Tyr Asp Glu Lys Val Gly Ile Tyr Asp
                165                 170
```

<210> SEQ ID NO 4
<211> LENGTH: 185
<212> TYPE: PRT
<213> ORGANISM: Neurospora crassa

<400> SEQUENCE: 4

```
Met Lys Phe Phe Ser Ala Leu Ala Leu Ser Ser Leu Leu Pro Thr Ala
1               5                   10                  15

Ala Trp Ala Trp Thr Gly Ser Glu Ser Asp Ser Thr Gly Ala Asp Ser
            20                  25                  30

Leu Phe Arg Arg Ala Glu Thr Ile Gln Gln Thr Thr Asp Arg Tyr Leu
        35                  40                  45

Phe Arg Ile Thr Leu Pro Gln Phe Thr Ala Tyr Arg Asn Ala Arg Ser
    50                  55                  60

Pro Ala Thr Leu Asp Trp Ser Ser Asp Ser Cys Ser Tyr Ser Pro Asp
65                  70                  75                  80

Asn Pro Leu Gly Phe Pro Phe Ser Pro Ala Cys Asn Arg His Asp Phe
                85                  90                  95

Gly Tyr Arg Asn Tyr Lys Ala Gln Ser Arg Phe Thr Asp Asn Asn Lys
            100                 105                 110

Leu Lys Ile Asp Gly Asn Phe Lys Thr Asp Leu Tyr Tyr Gln Cys Asp
        115                 120                 125

Thr His Gly Tyr Gly Ser Thr Cys His Ala Leu Ala Asn Val Tyr Tyr
    130                 135                 140

Ala Ala Val Arg Glu Phe Gly Arg Thr Lys Gly Glu Leu Gln Glu Glu
145                 150                 155                 160
```

-continued

```
Tyr Asp Leu Leu Leu Ala His Tyr Asn Glu Leu Val Ala Glu Ala Ile
                165                 170                 175

Ala Lys Gly Glu Asp Pro Leu Tyr Tyr
            180                 185


<210> SEQ ID NO 5
<211> LENGTH: 169
<212> TYPE: PRT
<213> ORGANISM: Helicosporium sp.

<400> SEQUENCE: 5

Met Lys Ser Phe Thr Phe Val Val Leu Ala Leu Leu Pro Phe Ser Ser
1               5                   10                  15

Ala Leu Pro Phe Gly Leu Phe His Arg Gly Gly Ile Ala Ser Arg Ala
            20                  25                  30

Thr Ile Glu Glu Thr Thr Asp Thr Leu Leu Phe Ser Thr Pro Ile Ala
        35                  40                  45

Gln Phe Glu Ala Ala Arg Asn Ala Gln Asn Pro Ser Thr Leu Asp Trp
    50                  55                  60

Ser Ser Asp Gly Cys Ser Ser Ser Pro Asp Asp Pro Phe Gly Phe Asp
65                  70                  75                  80

Phe Leu Ser Ser Cys His Arg His Asp Phe Gly Tyr Arg Asn Tyr Lys
                85                  90                  95

Lys Gln Asn Arg Phe Thr Ala Pro Asn Lys Ala Arg Ile Asp Thr Asn
            100                 105                 110

Phe Lys Thr Asp Met Tyr Asn Gln Cys Asn Thr Glu Ser Asn Ile Phe
        115                 120                 125

Thr Arg Ala Ala Cys Lys Ala Val Ala Asp Ile Tyr Tyr Glu Ala Val
    130                 135                 140

Lys Thr Phe Gly Ser Lys Lys Arg Ala Ala Glu Ala Leu Ala Ala Arg
145                 150                 155                 160

Gln Met Glu Glu Asn Val Ala Lys Ala
                165


<210> SEQ ID NO 6
<211> LENGTH: 942
<212> TYPE: DNA
<213> ORGANISM: Aspergillus oryzae
<220> FEATURE:
<221> NAME/KEY: CDS
<222> LOCATION: (61)..(726)

<400> SEQUENCE: 6

cgcaagcatc acatctactt cttattgcct attctgtccg agtgctagcc acttatcatc      60

atg aag aac atc ttc gtt gcc act ttg ggc ctg ttc gcc gca gtt tcg       108
Met Lys Asn Ile Phe Val Ala Thr Leu Gly Leu Phe Ala Ala Val Ser
1               5                   10                  15

tct gcc ttg ccc tac aca acc cct gtc aat gac aat ccc atc tct gct       156
Ser Ala Leu Pro Tyr Thr Thr Pro Val Asn Asp Asn Pro Ile Ser Ala
            20                  25                  30

tta caa gca cgc gcg aca aca tgc tcg gcc aag gcc acg gat aac ctc       204
Leu Gln Ala Arg Ala Thr Thr Cys Ser Ala Lys Ala Thr Asp Asn Leu
        35                  40                  45

atc ttc aag gtc tcc atg aag acc ttc cag aag gcg cgc aag gcc aag       252
Ile Phe Lys Val Ser Met Lys Thr Phe Gln Lys Ala Arg Lys Ala Lys
    50                  55                  60

aac ccc tcc aag tgc aac tgg tca tcg gac aac tgc tcc aag tca ccc       300
Asn Pro Ser Lys Cys Asn Trp Ser Ser Asp Asn Cys Ser Lys Ser Pro
65                  70                  75                  80
```

-continued

```
gat aag ccc gat gga tac aac ttc atc ccc agc tgc caa aga cac gat      348
Asp Lys Pro Asp Gly Tyr Asn Phe Ile Pro Ser Cys Gln Arg His Asp
                85                  90                  95

ttc ggc tac cgg aac acg aag aag cag aag cgc ttc aca aag gcc atg      396
Phe Gly Tyr Arg Asn Thr Lys Lys Gln Lys Arg Phe Thr Lys Ala Met
            100                 105                 110

aag aag cgc att gac gac aac ttc aag aag gat ctc tac aag tac tgc      444
Lys Lys Arg Ile Asp Asp Asn Phe Lys Lys Asp Leu Tyr Lys Tyr Cys
        115                 120                 125

agc caa ttc tcg ggc tgg agc tca tgg aag gga gtg gag tgc cgt cgc      492
Ser Gln Phe Ser Gly Trp Ser Ser Trp Lys Gly Val Glu Cys Arg Arg
    130                 135                 140

ctt gcg gat gtc tac tat act gct gtc cgc cac ttt ggc aag cgt gat      540
Leu Ala Asp Val Tyr Tyr Thr Ala Val Arg His Phe Gly Lys Arg Asp
145                 150                 155                 160

gaa gcg ctt gag ttt gac cct gag gtt gag ttc gag aag cgt gat gag      588
Glu Ala Leu Glu Phe Asp Pro Glu Val Glu Phe Glu Lys Arg Asp Glu
                165                 170                 175

gtg gcc gat gtc cag cct gac gaa ttt gat aac ttt gac ggt tct gaa      636
Val Ala Asp Val Gln Pro Asp Glu Phe Asp Asn Phe Asp Gly Ser Glu
            180                 185                 190

gtt gac cct gat atc gag ggc cag gtc att ccc gaa gtt ctt gaa gat      684
Val Asp Pro Asp Ile Glu Gly Gln Val Ile Pro Glu Val Leu Glu Asp
        195                 200                 205

gat gga gtg gat gtg gag aac ctc gac gat att gaa aac ctg              726
Asp Gly Val Asp Val Glu Asn Leu Asp Asp Ile Glu Asn Leu
    210                 215                 220

taggttttcg gcattggctc tacactttgc aaatgggtcg tcataatcca ttggaagccg    786

gaggaggagg gaaatcaagg catcttttgg ttgtcagtaa ctttgagtgc ctagtttgtg    846

aattgttttt tgaggttcta tttgaattct gcttttgttc aatcttatag cttcctacgt    906

tgttgtcatt taaaaatgga caggagtatc tgtgag                              942


<210> SEQ ID NO 7
<211> LENGTH: 222
<212> TYPE: PRT
<213> ORGANISM: Aspergillus oryzae

<400> SEQUENCE: 7

Met Lys Asn Ile Phe Val Ala Thr Leu Gly Leu Phe Ala Ala Val Ser
1               5                   10                  15

Ser Ala Leu Pro Tyr Thr Thr Pro Val Asn Asp Asn Pro Ile Ser Ala
            20                  25                  30

Leu Gln Ala Arg Ala Thr Thr Cys Ser Ala Lys Ala Thr Asp Asn Leu
        35                  40                  45

Ile Phe Lys Val Ser Met Lys Thr Phe Gln Lys Ala Arg Lys Ala Lys
    50                  55                  60

Asn Pro Ser Lys Cys Asn Trp Ser Ser Asp Asn Cys Ser Lys Ser Pro
65                  70                  75                  80

Asp Lys Pro Asp Gly Tyr Asn Phe Ile Pro Ser Cys Gln Arg His Asp
                85                  90                  95

Phe Gly Tyr Arg Asn Thr Lys Lys Gln Lys Arg Phe Thr Lys Ala Met
            100                 105                 110

Lys Lys Arg Ile Asp Asp Asn Phe Lys Lys Asp Leu Tyr Lys Tyr Cys
        115                 120                 125

Ser Gln Phe Ser Gly Trp Ser Ser Trp Lys Gly Val Glu Cys Arg Arg
    130                 135                 140
```

-continued

```
Leu Ala Asp Val Tyr Tyr Thr Ala Val Arg His Phe Gly Lys Arg Asp
145                 150                 155                 160

Glu Ala Leu Glu Phe Asp Pro Glu Val Glu Phe Glu Lys Arg Asp Glu
                165                 170                 175

Val Ala Asp Val Gln Pro Asp Glu Phe Asp Asn Phe Asp Gly Ser Glu
            180                 185                 190

Val Asp Pro Asp Ile Glu Gly Gln Val Ile Pro Glu Val Leu Glu Asp
        195                 200                 205

Asp Gly Val Asp Val Glu Asn Leu Asp Asp Ile Glu Asn Leu
    210                 215                 220


<210> SEQ ID NO 8
<211> LENGTH: 249
<212> TYPE: PRT
<213> ORGANISM: Neurospora crassa

<400> SEQUENCE: 8

Met Lys Pro Phe Phe Leu Ile Ser Leu Leu Val Thr Val Phe Met Ser
1               5                   10                  15

Leu Met Leu Ala Thr Thr Ala Gln Pro Ser Leu Pro Leu Asn Asn Arg
            20                  25                  30

Arg Glu Leu Ala Glu His Pro Pro Val Lys Gly Asn Pro Pro Asn Thr
        35                  40                  45

Gly Tyr Ala Leu Asp Trp Cys Lys Tyr Thr Ala Gly Met Leu Phe Gln
    50                  55                  60

Trp Asp Leu Pro Thr Phe Ile Lys His Arg Glu Ala Asn Phe Ser Leu
65                  70                  75                  80

Gly Arg Leu Thr Trp Asp Trp Ser Ser Asp Gly Cys Thr His Val Pro
                85                  90                  95

Asp Asn Pro Val Gly Phe Pro Phe Lys Pro Ala Cys Gln Arg His Asp
            100                 105                 110

Phe Gly Tyr Arg Asn Tyr Gln Val Gln Phe His Phe Thr Pro Arg Ala
        115                 120                 125

Arg Trp Lys Ile Asp Glu Asn Phe Leu Lys Glu Met Lys Phe Gln Cys
    130                 135                 140

Ile Gly His Asn Ile Phe Asn Ala Cys His Phe Met Ala His Val Tyr
145                 150                 155                 160

His Trp Gly Val Arg Thr Phe Tyr Lys Gly His Glu Gln Tyr Arg Glu
                165                 170                 175

Ser Glu Pro Ser His Lys Met Met Asp Thr Met Val Ala Ser Glu Ser
            180                 185                 190

Ser Asp Val Phe Asp Gly Met Asp Ala Asp Glu Ala Arg Asp Ala Leu
        195                 200                 205

Asn Pro Tyr Leu Ser Glu Glu Lys Thr Lys Glu Tyr Tyr Asp Arg Ala
    210                 215                 220

Leu Ala Arg Tyr Asn Lys Cys Val Glu Glu Ala Met Ala Gln Gly Ile
225                 230                 235                 240

Asp Leu Gln Lys Tyr Trp Ala Ala Phe
                245


<210> SEQ ID NO 9
<211> LENGTH: 832
<212> TYPE: DNA
<213> ORGANISM: Tuber albidum
<220> FEATURE:
<221> NAME/KEY: CDS
<222> LOCATION: (2)..(426)
```

-continued

```
<220> FEATURE:
<221> NAME/KEY: CDS
<222> LOCATION: (476)..(680)

<400> SEQUENCE: 9

a atg gtc aag att gct gcc att gtc ctc cta atg gga att cta gcc aat      49
  Met Val Lys Ile Ala Ala Ile Val Leu Leu Met Gly Ile Leu Ala Asn
  1               5                   10                  15

gct gcc gcc atc cct gtc agc gag cca gca gcc ctg gcg aag cgt gga       97
Ala Ala Ala Ile Pro Val Ser Glu Pro Ala Ala Leu Ala Lys Arg Gly
            20                  25                  30

aac gct gag gtc att gct gaa caa act ggt gat gtc ccg gat ttc aac      145
Asn Ala Glu Val Ile Ala Glu Gln Thr Gly Asp Val Pro Asp Phe Asn
        35                  40                  45

act caa att aca gag cca act ggg gag gga gac cgt ggg gat gtg gtc      193
Thr Gln Ile Thr Glu Pro Thr Gly Glu Gly Asp Arg Gly Asp Val Val
    50                  55                  60

gac gaa acc gat ttg tcc acg gat att gtc cca gag acc gag gct gct      241
Asp Glu Thr Asp Leu Ser Thr Asp Ile Val Pro Glu Thr Glu Ala Ala
65                  70                  75                  80

tcc ttc gcc gct agt tca gta tct gca gcc tca cca gca tct gac acc      289
Ser Phe Ala Ala Ser Ser Val Ser Ala Ala Ser Pro Ala Ser Asp Thr
                85                  90                  95

gac agg ctt ctc tac tca acc tcc atg ccc gcc ttc ttg act gct aag      337
Asp Arg Leu Leu Tyr Ser Thr Ser Met Pro Ala Phe Leu Thr Ala Lys
            100                 105                 110

cgc aat aag aac ccc ggc aac ttg gac tgg agc gat gat gga tgc agc      385
Arg Asn Lys Asn Pro Gly Asn Leu Asp Trp Ser Asp Asp Gly Cys Ser
        115                 120                 125

aac tcc ccg gac agg cct gca ggg ttt aac ttc ctt gac tc               426
Asn Ser Pro Asp Arg Pro Ala Gly Phe Asn Phe Leu Asp Ser
    130                 135                 140

gtaagtcctc cttcatttat gctatctaca ttcactaata ttcgaacag c tgc aag      482
                                                        Cys Lys

cgt cac gac ttc ggg tac cgc aac tac aag aag cag cgc cgc ttc aca      530
Arg His Asp Phe Gly Tyr Arg Asn Tyr Lys Lys Gln Arg Arg Phe Thr
145                 150                 155                 160

gag cct aat cgc aag cgc att gat gac aat ttc aag aag gac cta tat      578
Glu Pro Asn Arg Lys Arg Ile Asp Asp Asn Phe Lys Lys Asp Leu Tyr
              165                 170                 175

aat gag tgc gcc aag tac tct ggc ctc caa tcc tgg aaa ggt gtt gcc      626
Asn Glu Cys Ala Lys Tyr Ser Gly Leu Gln Ser Trp Lys Gly Val Ala
          180                 185                 190

tgc cgc aaa atc gcg aac act tac tac gat gct gta cgc tcc ttc ggt      674
Cys Arg Lys Ile Ala Asn Thr Tyr Tyr Asp Ala Val Arg Ser Phe Gly
      195                 200                 205

tgg ttg taaatgtgcg gaagagatat caagtgggat cgaggaagag gatggtgaaa       730
Trp Leu
  210

gagctgagag gtggatttct ttacattccg caatggctac tacagaagaa ctgtgctcct    790

caaatttaat ctcatttttg tgtctatcta tccactctag aa                       832


<210> SEQ ID NO 10
<211> LENGTH: 210
<212> TYPE: PRT
<213> ORGANISM: Tuber albidum
```

-continued

<400> SEQUENCE: 10

Met Val Lys Ile Ala Ala Ile Val Leu Leu Met Gly Ile Leu Ala Asn
1               5                   10                  15

Ala Ala Ala Ile Pro Val Ser Glu Pro Ala Ala Leu Ala Lys Arg Gly
            20                  25                  30

Asn Ala Glu Val Ile Ala Glu Gln Thr Gly Asp Val Pro Asp Phe Asn
        35                  40                  45

Thr Gln Ile Thr Glu Pro Thr Gly Glu Gly Asp Arg Gly Asp Val Val
    50                  55                  60

Asp Glu Thr Asp Leu Ser Thr Asp Ile Val Pro Glu Thr Glu Ala Ala
65                  70                  75                  80

Ser Phe Ala Ala Ser Ser Val Ser Ala Ala Ser Pro Ala Ser Asp Thr
                85                  90                  95

Asp Arg Leu Leu Tyr Ser Thr Ser Met Pro Ala Phe Leu Thr Ala Lys
            100                 105                 110

Arg Asn Lys Asn Pro Gly Asn Leu Asp Trp Ser Asp Asp Gly Cys Ser
        115                 120                 125

Asn Ser Pro Asp Arg Pro Ala Gly Phe Asn Phe Leu Asp Ser Cys Lys
    130                 135                 140

Arg His Asp Phe Gly Tyr Arg Asn Tyr Lys Lys Gln Arg Arg Phe Thr
145                 150                 155                 160

Glu Pro Asn Arg Lys Arg Ile Asp Asp Asn Phe Lys Lys Asp Leu Tyr
                165                 170                 175

Asn Glu Cys Ala Lys Tyr Ser Gly Leu Gln Ser Trp Lys Gly Val Ala
            180                 185                 190

Cys Arg Lys Ile Ala Asn Thr Tyr Tyr Asp Ala Val Arg Ser Phe Gly
        195                 200                 205

Trp Leu
    210

<210> SEQ ID NO 11
<211> LENGTH: 961
<212> TYPE: DNA
<213> ORGANISM: Verticillium tenerum
<220> FEATURE:
<221> NAME/KEY: CDS
<222> LOCATION: (5)..(628)

<400> SEQUENCE: 11 caac atg aag acc acc gct gtt ctc tcc ctc gcc atg ctc cag gcc acc 49
     Met Lys Thr Thr Ala Val Leu Ser Leu Ala Met Leu Gln Ala Thr
     1               5                   10                  15 tgg gcc tcg ccc gtg gcc aag cgc cag aac gac gtc tcc ctc gtc gac 97
Trp Ala Ser Pro Val Ala Lys Arg Gln Asn Asp Val Ser Leu Val Asp
                20                  25                  30 aac tac atg ttc ggc atc tcg ctg ccc acc ttc tcc aac cac cac tcc 145
Asn Tyr Met Phe Gly Ile Ser Leu Pro Thr Phe Ser Asn His His Ser
            35                  40                  45 aac agg aac ccc cct cgc ctg gac tgg acc acc gac ggc tgc acc tcg 193
Asn Arg Asn Pro Pro Arg Leu Asp Trp Thr Thr Asp Gly Cys Thr Ser
        50                  55                  60 tcg ccc aac aac ccg ctc ggc ttc ccc ttc ctg ccc gcc tgc cac cgc 241
Ser Pro Asn Asn Pro Leu Gly Phe Pro Phe Leu Pro Ala Cys His Arg
    65                  70                  75 cac gac ttt ggc tac cag aac ttc cgc atc cag agc cgc ttc acc cag 289
His Asp Phe Gly Tyr Gln Asn Phe Arg Ile Gln Ser Arg Phe Thr Gln
80                  85                  90                  95

-continued

```
agc aac aag ctc cgc atc gac gac aag ttc aag gag gac ctc tac cac      337
Ser Asn Lys Leu Arg Ile Asp Asp Lys Phe Lys Glu Asp Leu Tyr His
                100                 105                 110

cag tgc gac ggc cac tgg gcc tgg gtt gcc tgc gct gcc ctc gcc gag      385
Gln Cys Asp Gly His Trp Ala Trp Val Ala Cys Ala Ala Leu Ala Glu
            115                 120                 125

gtc tac tac gcc gcc gtc cgc gcc ttc ggc ggt ggt gac gcc acc ccg      433
Val Tyr Tyr Ala Ala Val Arg Ala Phe Gly Gly Gly Asp Ala Thr Pro
        130                 135                 140

gga cgc atg cac gtc gcc gtc ttc ggc cag acc cag gcc gag cac gac      481
Gly Arg Met His Val Ala Val Phe Gly Gln Thr Gln Ala Glu His Asp
    145                 150                 155

gcc ctc gtc tcc atc tac gag gag aag ctc gcg gcc tac gag gct gcc      529
Ala Leu Val Ser Ile Tyr Glu Glu Lys Leu Ala Ala Tyr Glu Ala Ala
160                 165                 170                 175

gtc gcc gag gcc gag gcc cgc ggc gag atc ccc cac gtc gag gag acc      577
Val Ala Glu Ala Glu Ala Arg Gly Glu Ile Pro His Val Glu Glu Thr
                180                 185                 190

ctc ccc gag gag cct gcc gcc gag gag ccc gcc gcc gag gag gag cag      625
Leu Pro Glu Glu Pro Ala Ala Glu Glu Pro Ala Ala Glu Glu Glu Gln
            195                 200                 205

aag taaacacgag ccccttttag gaccgactag ctcggtgtcg ctgggctagg           678
Lys

ctgagctgag tgacggggag gcacgaaaga gagcaatgca tcagacaggc tggaacatgc    738

ctttgtctga gtgatggatg gacttgatgg acttgatgga cttggatgca tttatgatac    798

cgccagtgtt gactggcaga gcgagcgact tgattttgga tttcttgaaa ggacggatgt    858

cccgaggtgg ataagggatg ccttatcacc aacttcttca tgtatatatt gtactgcgca    918

gagaagcgcg ccccgaaaaa tggattgatt cttgatgaga cgt                      961


<210> SEQ ID NO 12
<211> LENGTH: 208
<212> TYPE: PRT
<213> ORGANISM: Verticillium tenerum

<400> SEQUENCE: 12

Met Lys Thr Thr Ala Val Leu Ser Leu Ala Met Leu Gln Ala Thr Trp
1               5                   10                  15

Ala Ser Pro Val Ala Lys Arg Gln Asn Asp Val Ser Leu Val Asp Asn
            20                  25                  30

Tyr Met Phe Gly Ile Ser Leu Pro Thr Phe Ser Asn His His Ser Asn
        35                  40                  45

Arg Asn Pro Pro Arg Leu Asp Trp Thr Thr Asp Gly Cys Thr Ser Ser
    50                  55                  60

Pro Asn Asn Pro Leu Gly Phe Pro Phe Leu Pro Ala Cys His Arg His
65                  70                  75                  80

Asp Phe Gly Tyr Gln Asn Phe Arg Ile Gln Ser Arg Phe Thr Gln Ser
                85                  90                  95

Asn Lys Leu Arg Ile Asp Asp Lys Phe Lys Glu Asp Leu Tyr His Gln
            100                 105                 110

Cys Asp Gly His Trp Ala Trp Val Ala Cys Ala Ala Leu Ala Glu Val
        115                 120                 125

Tyr Tyr Ala Ala Val Arg Ala Phe Gly Gly Gly Asp Ala Thr Pro Gly
    130                 135                 140

Arg Met His Val Ala Val Phe Gly Gln Thr Gln Ala Glu His Asp Ala
145                 150                 155                 160
```

-continued

```
Leu Val Ser Ile Tyr Glu Glu Lys Leu Ala Ala Tyr Glu Ala Ala Val
                165                 170                 175

Ala Glu Ala Glu Ala Arg Gly Glu Ile Pro His Val Glu Glu Thr Leu
            180                 185                 190

Pro Glu Glu Pro Ala Ala Glu Glu Pro Ala Ala Glu Glu Glu Gln Lys
        195                 200                 205


<210> SEQ ID NO 13
<211> LENGTH: 29
<212> TYPE: DNA
<213> ORGANISM: Artificial
<220> FEATURE:
<223> OTHER INFORMATION: TbPLA1 primer
<220> FEATURE:
<221> NAME/KEY: misc_feature
<222> LOCATION: (4)..(9)
<223> OTHER INFORMATION: BamHI site

<400> SEQUENCE: 13

caaggatcca aaatggtcaa gattgctgc                                      29


<210> SEQ ID NO 14
<211> LENGTH: 34
<212> TYPE: DNA
<213> ORGANISM: Artificial
<220> FEATURE:
<223> OTHER INFORMATION: TbPLA2 primer
<220> FEATURE:
<221> NAME/KEY: misc_feature
<222> LOCATION: (4)..(9)
<223> OTHER INFORMATION: XhoI site

<400> SEQUENCE: 14

tgcctcgagt tttttctaga gtggatagat agac                                34


<210> SEQ ID NO 15
<211> LENGTH: 690
<212> TYPE: DNA
<213> ORGANISM: Fusarium venenatum
<220> FEATURE:
<221> NAME/KEY: CDS
<222> LOCATION: (49)..(597)

<400> SEQUENCE: 15

cagttttggt tctttccttc cttatccatc acttctagta tcttcaag atg aag ttc      57
                                                     Met Lys Phe
                                                     1

agc gct acc att ctt tca ctc ctc ccg gca gtt ctc gcc ctg ccc aca     105
Ser Ala Thr Ile Leu Ser Leu Leu Pro Ala Val Leu Ala Leu Pro Thr
    5                   10                  15

ggc gaa gat gca tct gtc tca aag cgc cag agc gtg aac aca gtg aca     153
Gly Glu Asp Ala Ser Val Ser Lys Arg Gln Ser Val Asn Thr Val Thr
20                  25                  30                  35

gat cag ctc ctc ttc agc gtc aca ctc cca caa ttc act gct cgt cgt     201
Asp Gln Leu Leu Phe Ser Val Thr Leu Pro Gln Phe Thr Ala Arg Arg
                40                  45                  50

aac gcc cgt gat cct ccc act gtc gac tgg acc tct gac ggt tgc act     249
Asn Ala Arg Asp Pro Pro Thr Val Asp Trp Thr Ser Asp Gly Cys Thr
            55                  60                  65

tcc tcg ccc gac aac cct ttc ggc ttc cct ttt atc cct gcc tgc aac     297
Ser Ser Pro Asp Asn Pro Phe Gly Phe Pro Phe Ile Pro Ala Cys Asn
        70                  75                  80
```

-continued

```
cgt cac gac ttt ggc tac cac aac tac cgc gcc cag agc cgc ttc acc      345
Arg His Asp Phe Gly Tyr His Asn Tyr Arg Ala Gln Ser Arg Phe Thr
    85                  90                  95

gtg agc gcc aag tcc cgc atc gac aac aac ttc aag acc gat ttg tac      393
Val Ser Ala Lys Ser Arg Ile Asp Asn Asn Phe Lys Thr Asp Leu Tyr
100                 105                 110                 115

ttc caa tgc caa tcc tcc agt gtt tct ggt gtc tgc aga gca ctt gcc      441
Phe Gln Cys Gln Ser Ser Ser Val Ser Gly Val Cys Arg Ala Leu Ala
                120                 125                 130

gac gtc tac ttc gcc gcg gtt aga gct ttt ggc ggg gat gat gct act      489
Asp Val Tyr Phe Ala Ala Val Arg Ala Phe Gly Gly Asp Asp Ala Thr
            135                 140                 145

cct ggc aag aga gat gag gcc ctt gta aag gag tac gaa aag aag gta      537
Pro Gly Lys Arg Asp Glu Ala Leu Val Lys Glu Tyr Glu Lys Lys Val
        150                 155                 160

gaa gtc tac aac aag ctt gtt gaa gag gct cag aag aag ggt gat ctc      585
Glu Val Tyr Asn Lys Leu Val Glu Glu Ala Gln Lys Lys Gly Asp Leu
    165                 170                 175

cct cgc ctt gac tagagtggtt caaaaagcat tctttgggtt cattgtacat          637
Pro Arg Leu Asp
180

aaatccttac gatacatgag ttatgataaa tcttaaatgg cgggtgacga gct           690


<210> SEQ ID NO 16
<211> LENGTH: 183
<212> TYPE: PRT
<213> ORGANISM: Fusarium venenatum

<400> SEQUENCE: 16

Met Lys Phe Ser Ala Thr Ile Leu Ser Leu Leu Pro Ala Val Leu Ala
1               5                   10                  15

Leu Pro Thr Gly Glu Asp Ala Ser Val Ser Lys Arg Gln Ser Val Asn
            20                  25                  30

Thr Val Thr Asp Gln Leu Leu Phe Ser Val Thr Leu Pro Gln Phe Thr
        35                  40                  45

Ala Arg Arg Asn Ala Arg Asp Pro Pro Thr Val Asp Trp Thr Ser Asp
    50                  55                  60

Gly Cys Thr Ser Ser Pro Asp Asn Pro Phe Gly Phe Pro Phe Ile Pro
65                  70                  75                  80

Ala Cys Asn Arg His Asp Phe Gly Tyr His Asn Tyr Arg Ala Gln Ser
                85                  90                  95

Arg Phe Thr Val Ser Ala Lys Ser Arg Ile Asp Asn Asn Phe Lys Thr
            100                 105                 110

Asp Leu Tyr Phe Gln Cys Gln Ser Ser Ser Val Ser Gly Val Cys Arg
        115                 120                 125

Ala Leu Ala Asp Val Tyr Phe Ala Ala Val Arg Ala Phe Gly Gly Asp
    130                 135                 140

Asp Ala Thr Pro Gly Lys Arg Asp Glu Ala Leu Val Lys Glu Tyr Glu
145                 150                 155                 160

Lys Lys Val Glu Val Tyr Asn Lys Leu Val Glu Glu Ala Gln Lys Lys
                165                 170                 175

Gly Asp Leu Pro Arg Leu Asp
            180
```